US008029989B2

(12) United States Patent
Chodosh

(10) Patent No.: US 8,029,989 B2
(45) Date of Patent: Oct. 4, 2011

(54) METHOD USING SNAIL TRANSCRIPTIONAL REPRESSOR

(75) Inventor: Lewis A. Chodosh, West Chester, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 196 days.

(21) Appl. No.: 11/991,052

(22) PCT Filed: Aug. 25, 2006

(86) PCT No.: PCT/US2006/033409
§ 371 (c)(1),
(2), (4) Date: Nov. 17, 2008

(87) PCT Pub. No.: WO2007/025231
PCT Pub. Date: Mar. 1, 2007

(65) Prior Publication Data
US 2009/0232819 A1    Sep. 17, 2009

Related U.S. Application Data

(60) Provisional application No. 60/711,645, filed on Aug. 26, 2005.

(51) Int. Cl.
*C12Q 1/68* (2006.01)
*G01N 33/53* (2006.01)

(52) U.S. Cl. .............................................. 435/6; 435/7.1
(58) Field of Classification Search ........................ None
See application file for complete search history.

(56) References Cited

U.S. PATENT DOCUMENTS

| | | | |
|---|---|---|---|
| 5,168,053 A | 12/1992 | Altman | |
| 5,190,931 A | 3/1993 | Inouye | |
| 5,223,409 A | 6/1993 | Ladner | |
| 5,403,484 A | 4/1995 | Ladner | |
| 5,571,698 A | 11/1996 | Ladner | |
| 6,004,490 A | 12/1999 | Tsai | |
| 6,328,709 B1 | 12/2001 | Hung | |
| 6,506,559 B1 | 1/2003 | Fire | |
| 2003/0224490 A1 | 12/2003 | Dessain | |
| 2005/0186668 A1 | 8/2005 | Chodosh | |

OTHER PUBLICATIONS

Elloul et al (Cancer, 2005, 103(8): 1631-1643).*
Asgeirsson et al (European Journal of Cancer, 2000, 36: 1098-1106).*
Altschul et al., "Basic Local Alignment Search Tool", J. Mol. Biol. 215:403-410 (1990).
Altschul et al. "Gapped BLAST and PSI-BLAST: a new generation of protein database search programs," Nucleic Acids Res. 25:3389-3402 (1997).
American Cancer Society, Breast Cancer Facts & Figures 2003, Atlanta, GA, pp. 1-27 (2003).
Bachelder et al., "Glycogen synthase kinase-3 is an endogenous inhibitor of Snail transcription: implications for the epithelial- . . . " J. Cell Biol. 168: 29-33 (2003).
Barallo-Gimeno et al., "The Snail genes as inducers of cell movement and survival: implications in development and cancer," Development 132:3151-3161 (2005).
Barbas, "Synthetic Human Antibodies," Nat. Med. 1:837-839 (1995).
Barbera et al., "Regulation of Snail transcription during epithelial to mesenchymal transition of tumor cells," Oncogene 23:7345-7354 (2004).
Baselga et al., "Phase II Study of Weekly Intravenous Recombinant Humanized Anti-p185HER2 Monoclonal Antibody in Patients With HER2/neu- . . . " J. Clin. Oncol. 14:737-744 (1996).
Batlle et al., "The transcription factor Snail is a repressor of E-cadherin gene expression in epithelial tumour cells," Nat. Cell Biol. 2:84-89 (2000).
Beerli et al. "Inhibition of Signaling from Type 1 Receptor Tyrosine Kinases via Intracellular Expression of Single-Chain Antibodies," Breast Cancer Res.Treat. 38:11-17 (1996).
Berg et al., "The Galvanization of Biology: A Growing Appreciation for the Roles of Zinc," Science 271:1081-1085 (1996).
Berger et al., "Correlation of c-erbB-2 Gene Amplification and Protein Expression in Human Breast Carcinoma with Nodal Status and Nuclear . . . " Cancer Res. 48:1238-1243 (1988).
Bird et al., "Single-Chain Antigen-Binding Proteins," Science 242:423-426 (1988).
Blanco et al., "Correlation of Snail expression with histological grade and lymph node status in breast carcinomas," Oncogene 21:3241-3246 (2002).
Burton et al., "Human Antibodies from Combinatorial Libraries," Adv. Immunol. 57:191-280 (1994).
Cano et al., "The transcription factor Snail controls epithelial-mesenchymal transitions by repressing E-cadherin expression," Nat Cell Biol. 2:76-83 (2000).
Cardiff et al., "Transgenic Oncogene Mice," Amer. J. Pathol. 139:495-501 (1991).
Cardiff et al., "The mammary pathology of genetically engineered mice: the consensus report and recommendations from the Annapolis meeting{," Oncogene 19:968-988 (2000).
Carell et al., "A Novel Procedure for the Synthesis of Libraries Containing Small Organic Molecules," Angew. Chem. Int. Ed. Engl. 33:2059-2061 (1994).
Carell et al., "A Solution-Phase Screening Procedure for the Isolation of Active Compounds from a Library of Molecules," Angew. Chem. Int. Ed. Engl. 33:2061-2064 (1994).

(Continued)

*Primary Examiner* — Sean Aeder
(74) *Attorney, Agent, or Firm* — Montgomery, McCracken, Walker & Rhoads, LLP; Evelyn H. McConathy

(57) ABSTRACT

Provided is a prognostic molecular marker for breast cancer recurrence. Expression of Snail, a zinc finger transcriptional repressor gene, is correlated to the risk of breast cancer recurrence, and to the likelihood of recurrence-free survival in subjects diagnosed with breast cancer. Further provided are methods of identifying therapeutic compositions for treating breast cancer to reduce recurrence associated with high expression of Snail, and methods of controlling Snail expression for research and therapeutic purposes.

7 Claims, 7 Drawing Sheets

OTHER PUBLICATIONS

Carter et al., "Relation of Tumor Size, Lymph Node Status, and Survival in 24,740 Breast Cancer Cases," Cancer 63:181-187 (1989).

Carver et al., "The Mouse Snail Gene Encodes a Key Regulator of the Epithelial-Mesenchymal Transition," Mol. Cell Biol. 21:8184-8188 (2001).

Cech, "Ribozymes and Their Medical Implications," J. Amer. Med. Assn. 260:3030-3034 (1988).

Cech et al., "RNA Catalysis by a Group I Ribozyme," J. Biol. Chem. 267:17479-17482 (1992).

Cheng et al., "Mechanisms of inactivation of E-cadherin in breast carcinoma: modification of the two-hit hypothesis of tumor suppressor gene," Oncogene 20:3814-3823 (2001).

Cho et al., "An Unnatural Biopolymer," Science 261:1303-1305 (1993).

Cobleigh et al., "Multinational Study of the Efficacy and Safety of Humanized Anti-HER2 Monoclonal Antibody in Women Who Have HER2-Over . . . " J. Clin Oncol. 17:2639-2648 (1999).

Coradini et al., "Biomolecular prognostic factors in breast cancer," Curr. Opin. Obstet. Gynecol. 16:49-55 (2004).

Cull et al., "Screening for receptor ligands using large libraries of peptides linked to the C terminus of the lac repressor," Proc. Natl. Acad. Sci. USA 89:1865-1869 (1992).

Cwirla et al., "Peptides on phage: A vast library of peptides for identifying ligands," Proc. Natl. Acad. Sci. USA 87:6378-6382 (1990).

D'Cruz et al., "tuc-MYC induces mammary tumorigenesis by means of a preferred pathway involving spontaneous Kras2 mutations," Nat. Med. 7:235-239 (2001).

De Craene et al., "The Transcription Factor Snail Induces Tumor Cell Invasion through Modulation of the Epithelial Cell Differentiation . . . ," Cancer Res. 65:6237-6244 (2005).

De Craene et al., "Unraveling signalling cascades for the Snail family of transcription factors," Cell Signal 17:535-547 (2005).

De Kruif et al., "Selection and Application of Human Single Chain Fv Antibody Fragments from a Semi-synthetic Phage Antibody Display . . . " J. Mol. Biol. 248:97-105 (1995).

Demicheli et al., "Menopausal status dependence of the timing of breast cancer recurrence after surgical removal of the primary tumour, "Breast Cancer Res. 6:689-696 (2004).

Devlin, "Random Peptide Libraries: A Source of Specific Protein Binding Molecules," Science 249:404-406 (1990).

Dewitt et al., ""Diversomers": An approach to nonpeptide, nonoligomeric chemical diversity," Proc. Natl. Acad. Sci. USA 90:6909-6913 (1993).

Doyle et al., "Long-Term Results of Local Recurrence After Breast Conservation Treatment for Invasive Breast Cancer," Int. J. Radiat. Oncol. Biol. Phys. 51:74-80 (2001).

Elloul et al., "Snail, Slug, and Smad-Interacting Protein 1 as Novel Parameters of Disease Aggressiveness in Metastatic Ovarian and Breast Carcinoma," Cancer 103(8):1631-1643.

Erb et al., "Recursive deconvolution of combinatorial chemical libraries," Proc. Natl. Acad. Sci. USA 91:11422-11426 (1994).

Esteva et al., "Prognostic molecular markers in early breast cancer," Breast Cancer Res. 6:109-118 (2004).

Felici, "Selection of Antibody Ligands from a Large Library of Oligopeptides Expressed on a Multivalent Exposition Vector," J Mol. Biol. 222:301-310 (1991).

Fentiman et al., "Long-term follow-up of the first breast conservation trial: Guy's wide excision study," Breast 9:5-8 (2000).

Fire et al., "Potent and specific genetic interference by double-stranded RNA in *Caenorhabditis elegans*," Nature 391(19):806-811 (1998).

Fisher et al., "Significance of Ipsilateral Breast Tumour Recurrence After Lumpectomy," Lancet 338:327-331 (1991).

Fisher et al., "Treatment of lymph-node-negative, oestrogen-receptorpositive breast cancer: long-term findings from National Surgical . . . " Lancet 364:858-868 (2004).

Fodor, "Multiplexed Biochemical Assays with Biological Chips," Nature 364:555-556 (1993).

Fortin et al., "Local Failure Is Responsible for the Decrease in Survival for Patients With Breast Cancer Treated With Conservative . . . " J. Clin. Oncol. 17:101-109 (1999).

Gallop et al., "Applications of Combinatorial Technologies to Drug Discovery. 1. Background and Peptide Combinatorial Libraries," J. Med. Chem. 37:1233-1251 (1994).

Grau et al., Mutations and Chromosomal Rearrangements Affecting the Expression of Snail, A Gene Involved in Embryonic Patterning Genetics. 108:347-360 (1984).

Gu et al., "Synergistic activation of transcription byCBPand p53," Nature. 387:819-823 (1997).

Gu et al., "Construction and Expression of Mouse-Human Chimeric Antibody SZ-51 Specific for Activated Platelet P-Selectin," Thrombosis and Hematocyst 77(4):755-759 (1997).

Guatelli et al., "Isothermal, in vitro amplification of nucleic acids by a multienzyme reaction modeled after retroviral . . . ," Proc. Natl. Acad. Sci. USA 87:1874-1878 (1990).

Gunther et al., "A novel doxycycline-inducible system for the transgenic analysis of mammary gland biology," Faseb J. 16:283-292 (2002).

Hajra et al., "The SLUG Zinc-Finger Protein Represses E-Cadherin in Breast Cancer1," Cancer Res. 62:1613-1618 (2002).

Hampel et al., "RNA Catalytic Properties of the Minimum (−)sTRSV Sequence," Biochemistry 28:4929-4933 (1989).

Hortobagyi et al., "Overview of Treatment Results With Trastuzumab (Herceptin) in Metastatic Breast Cancer," Semin. Oncol. 28:43-47 (2001).

Houghten, The Use of Synthetic Peptide Combinatorial Libraries of the Identification of Bioactive Peptides, Bio/Techniques 13:412-421 (1992).

Huston et al., "Protein engineering of antibody binding sites: Recovery of specific activity in an anti-digoxin single- . . . ," Proc. Natl. Acad. Sci. USA 85:5879-5883 (1988).

Karlin et al., "Methods for assessing the statistical significance of molecular sequence features by using general scoring . . . ," Proc. Natl. Acad. Sci. USA 87:2264-2268 (1990).

Karlin et al., "Applications and statistics for multiple high-scoring segments in molecular sequences," Proc. Natl. Acad. Sci. USA 90:5873-5877 (1993).

Katoh et al., "Identification and Characterization of Human SNAIL3 (SNAI3) gene in silico," Int. J. Mol. Med. 11, 383-388 (2003).

Kwoh et al., "Transcription-based amplification system and detection of amplified human immunodeficiency virus type 1 . . . ," Proc. Natl. Acad. Sci. USA 86:1173-1177 (1989).

Lam, "Application of Combinatorial Library Methods in Cancer Research and Drug Discovery," Anticancer Drug Des. 12:145 (1997).

Lam, "A new type of synthetic peptide library for identifying ligand-binding activity," Nature 354:82-84 (1991).

Lizardi et al., "Exponential Amplification of Recombinant-RNA Hybridization probes," Bio/Technology 6:1197 (1988).

Ma et al., "A two-gene expression ratio predicts clinical outcome in breast cancer patients treated with tamoxifen," Cancer Cell. 5:607-616 (2004).

Marcus-Sekura, "Techniques for Using Antisense Oligodeoxyribonucleotides to Study Gene Expression," Anal. Biochem. 172:289 (1988).

Marks et al., "Human Antibodies from V-gene Libraries Displayed on Phage," J. Mol. Biol. 222:581-597 (1991).

Master et al., "Genomic analysis of early murine mammary gland development using novel probe-level algorithms," Genome Biology. 6:R20, 2005 (2004).

Mistili et al., "Applications of the green fluorescent protein in cell biology and biotechnology," Nature Biotechnology 15:961-964 (1997).

Montgomery et al., "Double-stranded RNA as a mediator in sequence-specific genetic silencing and co-suppression," TIG 14(7):255-258 (1998).

Moody et al., "Conditional activation of Neu in the mammary epithelium of transgenic mice results in reversible pulmonary metastasis," Cancer Cell 2:451-461 (2002).

Pantel et al., "Detection and Clinical Implications of Early Systemic Tumor Cell Dissemination in Breast Cancer," Clin. Cancer Res. 9(17):6326-34 (2003).

Pantel et al., "Occult micrometastasis: enrichment, identification and characterization of single disseminated tumour cells," Semin. Cancer Biol. 11:327-337 (2001).

Parkin et al., "Global Cancer Statistics, 2002," CA Cancer J. Clin. 55:74-108 (2005).

Paznekas et al., "Genomic Organization, Expression, and Chromosome Location of the Human SNAIL Gene (SNAI1) and a Related Processed Pseudogene . . . ," Genomics 62:42-49 (1999).

Peinado et al., "Snail Mediates E-Cadherin Repression by the Recruitment of the Sin3A/Histone Deacetylase 1 (HDAC1)/HDAC2 Complex." Mol. Cell. Biol. 24:306-319 (2004).

Rajan et al., "Brca2 is coordinately regulated with Brca1 during proliferation and differentiation in mammary epithel- . . . ," Proc. Natl. Acad. Sci. U.S.A. 93:13078-13083 (1996).

Retsky et al., "Recent translational research: computational studies of breast cancer," Breast Cancer Res. 7:37-40 (2005).

Retsky et al., "Premenopausal status accelerates relapse in node positive breast cancer: hypothesis links angiogenesis . . . ," Breast Cancer Res. Treat. 65:217-224 (2001).

Saphner et al., "Annual Hazard Rates of Recurrence for Breast Cancer After Primary Therapy," J. Clin. Oncol. 14:2738-2746 (1996).

Schairer et al., "Probabilities of Death From Breast Cancer and Other Causes Among Female Breast Cancer Patients," J Natl. Cancer Inst. 96:1311-1321 (2004).

Schlotter et al., "C-myc, not HER-2/neu, can predict recurrence and mortality of patients with node-negative breast cancer," Breast Cancer Res. 5:R30-36 (2003).

Schmoor et al., "Role of Isolated Locoregional Recurrence of Breast Cancer: Results of Four Prospective Studies," J. Clin. Oncol. 18:1696-1708 (2000).

Scott et al., "Searching for Peptide Ligands with an Epitope Library," Science 249:386-390 (1990).

Slamon et al., "Use of Chemotherapy Plus a Monoclonal Antibody Against HER2 for Metastatic Breast Cancer That Overexpresses HER2," N. Engl. J. Med. 344:783-792 (2001).

Slamon et al., "Human Breast Cancer: Correlation of Relapse and Survival with Amplification of the HER-2/ne Oncogene," Science 235:177-182 (1987).

Solakoglu et al., "Heterogeneous proliferative potential of occult metastatic cells in bone marrow of patients with . . . ," Proc. Natl. Acad. Sci. U. S. A.99(4):2246-51 (2002).

Sorlie et al., "Gene expression patterns of breast carcinomas distinguish tumor subclasses with clinical implications," Proc. Natl. Acad. Sci. USA 98:10869-10874 (2001).

Sorlie et al. "Repeated observation of breast tumor subtypes in independent gene expression data sets," Proc. Natl. Acad. Sci. USA 100:8418-8423 (2003).

Soutschek et al., "Therapeutic silencing of an endogenous gene by systemic administration of modified siRNAs," Nature 432:173-178 (2004).

Tang et al., "The Akt Proto-oncogene Links Ras to Pak and Cell Survival Signals," J. Biol. Chem. 275: 9106-9109 (2000).

Thurm et al., "Rare Expression of Epithelial Cell Adhesion Molecule on Residual Micrometastatic Breast Cancer Cells after Adjuvant . . . ," Clin. Cancer Res. 9(7):2598-604 (2003).

Timmons et al., "Specific interference by ingested dsRNA," Nature 395:854 (1998).

Tuszynski et al. "Thrombospondin Promotes Platelet Aggregation Blood," Blood, 72:109-115 (1988).

Valagussa et al., "Patterns of Relapse and Survival Following Radical Mastectomy," Cancer 41:1170-1178 (1978).

Van't Veer et al. "Gene expression profiling predicts clinical outcome of breast cancer" Nature. 415:530-536 (2002).

Veronesi et al., "Local Recurrences and Distant Metastases After Conservative Breast Cancer Treatments: Partly Independent Events," J. Natl. Cancer Inst. 87:19-27 (1995).

Vincent-Salomon et al., "Host microenvironment in breast cancer development Epithelial-mesenchymal transition in breast cancer devel- . . . ," Breast Cancer Res. 5:101-106 (2003).

Vogel et al., "Efficacy and Safety of Trastuzumab as a Single Agent in First-Line Treatment of HER2-Overexpressing Metastatic Breast Cancer," J. Clin. Oncol. 20:719-726 (2002).

Wang et al. "Gene-expression profiles to predict distant metastasis of lymph-node-negative primary breast cancer," Lancet 365:671-679 (2005).

Wang et al., "HER2 Overexpression and Cancer Targeting," Semin. Oncol. 28:115-124 (2001).

Wang et al., "Targeting HERZ: Recent Developments and Future Directions for Breast Cancer Patients," Semin. Oncol. 28:21-29 (2001).

Weiss et al., "Natural History of More Than 20 Years of Node-Positive Primary Breast Carcinoma Treated With Cyclophosphamide, Metho- . . . ," J. Clin. Oncol. 21:1825-1835 (2003).

Wright et al. "Genetically Engineered Antibodies: Progress and Prospects," Critical Rev. Immunol. 12(3,4):125-168 (1992).

Yang et al., "Pak1 Phosphorylation of Snail , a Master Regulator of Epithelial-to-Mesenchyme Transition, Modulates Snail's Subcellular . . . ," Can. Res. 65: 3179-3184 (2005).

Zhou et al., Dual regulation of Snail by GSK-3β-mediated phosphorylation in control of epithelial—mesenchymal transition, Nature Cell Biol. 6: 931-940 (2004).

Zuckermann et al., "Discovery of Nanomolar Ligands for 7-Transmembrane G-Protein-Coupled Receptors from a Diverse N-(Substituted)glycine . . . ," J. Med. Chem. 37:2678-2685 (1994).

* cited by examiner

A

B

A

B

C

D

SEQUENCE LISTING

<160> NUMBER OF SEQ ID NOS: 5

<210> SEQ ID NO 1
<211> LENGTH: 7761
<212> TYPE: DNA
<213> ORGANISM: Homo sapiens
<220> FEATURE:
<221> NAME/KEY: misc_feature
<222> LOCATION: (1494)...(1494)
<223> OTHER INFORMATION: n: nucleotide identity not known

<400> SEQUENCE: 1

| | | | | | | |
|---|---|---|---|---|---|---|
| ggatcctgat | tggagctaaa | ttgacacggg | acggggagta | ttccgcttaa | tgactgctta | 60 |
| ctgcctctgt | ccccaccct | tactgcccgc | tctccagcta | gaaccagggg | aggacgattt | 120 |
| tgttcacggc | tgtcacaccc | ggcaccaagt | gactaaacag | acagtagttc | tgcccttcag | 180 |
| gttggtggtg | gtggtggtgt | ggggtgctta | taggttttta | tagtcttcct | tcacaggtgg | 240 |
| aaacaagaac | ggtgagacct | gtgaggttta | tttcagagcc | accccgggc | ctggtacgcc | 300 |
| tcccagggaa | gctggggtgg | gggtgcagct | gcccctcact | tgggcccacc | ccacatgcat | 360 |
| tcagtcaggg | ccctatgga | gccgtgttac | agcctttaga | cacaggatcg | aggatcttca | 420 |
| cggggtgagg | agacacgccc | ggcccatgcc | ttctttctcc | caccagccta | cagggatctt | 480 |
| tttcaacgaa | actctaacca | ggtccctcct | cagctgaaaa | tccttcggtg | gctcccagt | 540 |
| gcccttgagg | caaagtccaa | actcctacga | ggccctgggg | cccagcacat | ctgacccctc | 600 |
| cgggcatgcc | catcccaccc | catccctgga | agctgctctc | taggagttac | tctgaagcag | 660 |
| ttgccacttc | ttccctcggg | ccttttccct | tgataattct | tcacttcctc | tgggaagtca | 720 |
| ccccgacccc | ctgtcaggtg | acccgcctct | taacggtcgc | cgcgtcccgt | ctctccccca | 780 |
| ccaaagcaca | cttccctttg | cattgtaatt | atcctgtttac | ttcgtctgtc | tccctcactg | 840 |
| gaccagaagc | taccctttcgg | gagaggctct | gagtgttctg | tccggggctg | tgccctggcc | 900 |
| ccaggtacag | tgccccacac | gtgctgggcg | ctccgtaaac | actggataag | ggaaggaacg | 960 |
| ggtgctcttg | gctagctggg | ccaggctgct | ttgcaaaaag | gccgtggcat | tcaagccgc | 1020 |
| cgagagccac | gtgcggtgtc | cctttcctcg | cttcctcccc | agtgatgtgc | gtttccctcg | 1080 |
| tcaatgccac | gctctccagg | cgccagccgg | gcggaggaaa | tttccgcccc | ctcccaagcc | 1140 |
| cgaggcgggg | gcgggcgtcg | gaaggtcagg | tgtcccggcc | ggcgcgcagc | gccaggggc | 1200 |
| gtcagaagcg | ctcagaccac | cgggcgctga | gccggtgggc | gcgcggcgtc | ctgccggggt | 1260 |
| cccacctcgc | agaggcctcg | cttcgctcga | cgtcccgccc | cggacagccc | cagcaccggg | 1320 |
| gacgacccgc | gctgcgccag | cgaaccccgc | ctcggaggag | tccccgcccg | ggctctcacc | 1380 |
| gccacgcggc | gcgagcccgg | ccagcagccg | gcgcacctgc | tcggggagtg | gccttcggcg | 1440 |
| gagacgagcc | tccgattggc | gcggaggtga | caaaggggcg | tggcagataa | ggcnccggcc | 1500 |
| cctcccaccc | ccaccaccc | cccggagtac | ttaagggagt | tggcggcgct | gctgcattca | 1560 |
| ttgcgccgcg | gcacggccta | gcgagtggtt | cttctgcgct | actgctgcgc | gaatcggcga | 1620 |
| ccccagtgcc | tcgaccacta | tgccgcgctc | tttcctcgtc | aggaagccct | ccgacccaa | 1680 |
| tcggaagcct | aactacagcg | agctgcagga | ctctaatcca | ggtgcgttgg | aggggttctg | 1740 |
| ggctccagga | ggtttgggg | agacaggcga | aggctgcgtg | ggggcacct | gagggaggcg | 1800 |
| gcctgcctga | gccaggatcg | agtcacagga | tgttttgtgg | accattgcgg | gctcgggaga | 1860 |
| ccgggcaagt | gggtccccag | ttccggggat | ctgtctgggt | ggttggggga | gtgccgtgta | 1920 |

```
gagggcaggg gtcttcagct tgggggcct ttgtagccgg cgagaggcgg aggagctccg    1980
caagagggga aggagaggag gcctgtgtca ggagggccct ctggacgctg ctggggagag    2040
tccggagtcc agagggttga gggagggggt gggagacga gatgtgtgtg aggaggggga    2100
ttggggcagg gtggtggctc cggggctggg atgatgggt tctggcctca ggctggagac    2160
tggggactta ggagagggag atcaggaaat gacctccttc aactgggggt cctacgtgtg    2220
agagactcag attgggtgac ctgggcgagg agggcaggaa cctggtctgt cctgtggata    2280
atttttttga tctaattatg tattgagaat cggccccacc cagcccctgg ccagcggtgg    2340
gctcatgttt gttgattgag tgaatgattt aattaacgcc tgactctgct ttttctccct    2400
cagagtttac cttccagcag ccctacgacc aggcccacct gctggcagcc atcccacctc    2460
cggagatcct caaccccacc gcctcgctgc caatgctcat ctgggactct gtcctggcgc    2520
cccaagccca gccaattgcc tgggcctccc ttcggctcca ggagagtccc agggtggcag    2580
agctgacctc cctgtcagat gaggacagtg ggaaaggctc ccagccccc agcccaccct    2640 caccggctcc ttcgtccttc tcctctactt cagtctcttc cttggaggcc gaggcctatg    2700
ctgccttccc aggcttgggc caagtgccca agcagctggc ccagctctct gaggccaagg    2760
atctccaggc tcgaaaggcc ttcaactgca aatactgcaa caaggaatac ctcagcctgg    2820
gtgccctcaa gatgcacatc cgaagccaca cgctgcctg cgtctgcgga acctgcggga    2880
aggccttctc taggccctgg ctgctacaag gccatgtccg acccacact ggtacgtgcc    2940 cctccaggcg ccccaccgt tgctctctct ggcagctttt gtgaatctgg gcttgctgtt    3000
ctcattccca aagctgtgga cactgaggcc ccgagtcttc taacttctag ctcaagttcc    3060
agggcctggc tctctggaaa cgtttggcag aaactttctt catcagctaa gcagatgggc    3120
aaagcagaca ccttcccaat cccctgcagc ctgtttctca gccaaatggg tcggagctgg    3180
atatgggaaa ggtgcaacca acaccttgct gtggggcca ggtgtgaagg gcccacccg    3240 gccacaccct ctcccgggtc cgcccctcc ctagccagac aggatgttgt cagaccccc    3300 gcctggctct gaatccttct ttgagaactt tctcaaaact taggctgatg tttctcttct    3360
gtgagcctca ttttctctat cttctcagatg gcatgagaa cagcttttgg ggtttctata    3420
caggctaaat gcaggaatgc atatgggaag cacctggcaa agtgccggta cctgctaaac    3480
tctcacaaaa atggttcctt ggcatttgct ctgcttcctt gctgtgtgac tttgggcaag    3540
caacttaacc tctctgagcc ttaggggaaa actatgatag catatgtttt agagagtggc    3600
tgtaaaggtg gctaatcact ttatagtaat ttattatacc cgaacggttc tcaggtcggc    3660
ttccccaccc ccactgaatc ctagcacaca gaccaggaaa cggcatcttt ggggcagaaa    3720
acacaatcac gtcttttgaa aatttactaa atgtgtaaaa aactttctgg acatggaaaa    3780
aaggtagaac ttttttagaac ttgaatggtg gcagccactg tgcctggagc tgctctttgg    3840
agagtgacag ttgagggaga agattccaca gggttcaagc tggccaggtt ctgccatttc    3900
ctggcctggc gcctgacctc tgagcggtga gggttagtga ggtgtctggg aggactggca    3960
attcgcgggc tttattggca tcttattcga ctaaggctac ccatttctct tccttcgtgc    4020
accaattgct ctgattttaa catgtaaagg tccaactgcc tggcctcctg ggtgcctgcc    4080
cagctcacag ggctctatt tgggacagtt gaacccctca gggtgctgca gtcctgcctg    4140
cctctctcac ctcccatctg gacattattt taatgtaaag gcatggctga gacacagaaa    4200
tccccttgaa atgtatcatt gcggtcctca ttgactccca ttgtgtgcct taatggtggg    4260
cccagtgggt gggggctggg aggggtggag caggtgcatg gggcagcggt gcccagcacc    4320
```

```
tgttccagtc acagctgctg gcccactgca tggcaggccc ctttaatccg gggatatcgc    4380
atgtacagtg cccccctcgg cgcccttttgt ccccgccggc ctggtgccga tttcacactt   4440
gccaggagta ccatgaaggc gtctgggggg cgagggatcc aaggagtggg ggtctgtgcc   4500
tcctgcgtgt gcacacagcc cccgccccca gcccatcatg tcctagaatg tctccttccc   4560
cttttgtttg ggttcaggtc tcatcacact ttgggcactt actgtacagg agggtagtgc   4620
tcaggacttc accaacagcc ctgggaaggg aagggaggtg ctgtcctaac tctggtctta   4680
caaatggact ccagccccctt ttccagatct ccagagtcag cccttagttc acaagggtga   4740
acttaccctt ctcattcaca tgaagactta gaatgcaatc aacaaaccct tcaggcgtgg   4800
cgtgtggagg ctgctgagta atggcagagt ggagtagtgc tcaggcaccc ctcccccaat   4860
cctctatgtc ccccacccctt tggagtggcg agtttccatt tctgccccat gagactgagt   4920
ccagctctca ggcgctccat aagtccctat tgaatgcatg ggtcccattg gagccatcct   4980
ctggactctc tcctaccctg gtagctcagt gtggcaccct aggcacccag gaggtgatgg   5040
aatgaattca ctctcagctc ttaaattcca tccagcgctg ggatttcaca ggcgggccct   5100
gaccttgcgg gcatatcaga ctgggcgtga ggggattgga gaattgcatg ttttttaaaa   5160
agactattca gtattatgga atagtgtcta gcacttagta ggagctcagt agattaaaaa   5220
aaaaattata gacagggtct tgctttatcg cctaggcttg tctcaaactc ctggcttcaa   5280
gcaatcctgc ctcactcggc ctcccagagt gatgggatta caagcgtgag ccaccacacc   5340
cagcctcaat agattttttgt ttaatggggtt actgttatga cctttttattt ggaaaatgct   5400 gcatccccca gaaaaaaaca aatcaacatt attggtgttt ttggaactat atagcttttt   5460
ggttggagca gggattgtta tgaggcatga gtgaggggc agactcctct gaggcctctt   5520 taattttttaa aacagactta tttattctct aagggcttgt tgaggattta ctgggcaccc   5580
agctccatgt gcaagacttt tcccaacaca gccttggcca ggcagatggt gtgtcagggc   5640
cacaggtttc cgtagcctct tgggtgatag aaagggggccc aggccctggg ctggggctca   5700
gaagggactc aaaggaggcc cttgcccctta tgggactcag cctgattgga gaacagacaa   5760
ggagatttgg gattacagcg caggaggtgg ggtggtgagg aaagcaggct gctggccggg   5820
ccccaggagt ggcctaacca gcttggaggt gggggtgggg aagcctctta aggctgactc   5880
tggctttggc ccccaacaga gtaaatcaag gaatgactcc aggactgatg gtaaggacac   5940
cagtcacgtc ctcccttgac tgaaggcagt aagggcagta ggtgaaatca gaggctttgg   6000
ggtcctgcca ggggaacctg aacatgctac ttctgggcct cagtttcact gtctctgaaa   6060
tgagaccaca gtaggatcaa gtgacagtag gatgaatcag taaaggtgtt gagtcattgt   6120
tgaccacttc gcacgtccct gcgggatgtg gatgagtacc ctaccttctg tcacttatca   6180
acccctatga gtggggggtg aatagcccca ttttacaggt gggaaaatgg aggctcagag   6240
aagccagaca acttgctcag agttgcacag tgggaagcag cagagctccg tcaggtcccg   6300
gcctttggac cctggctgtg tgtttgacgg aggcctggct ttcctgggat catgggattc   6360
tttcagggtt tggggtatgc ggggagggat tccatcact gccagccgtt gtcccacggc   6420
tcactcggcc tttctggcgt tctctcccca ggcgagaagc ccttctcctg tccccactgc   6480
agccgtgcct tcgctgaccg ctccaacctg cgggcccacc tccagaccca ctcagatgtc   6540
aagaagtacc agtgccaggc gtgtgctcgg accttctccc gaatgtccct gctccacaag   6600
caccaagagt ccggctgctc aggatgtccc cgctgaccct cgaggctccc tcttcctctc   6660
catacctgcc cctgcctgac agccttcccc agctccagca ggaaggaccc cacatccttc   6720
```

```
tcactgccat ggaattccct cctgagtgcc ccacttctgg ccacatcagc cccacaggac    6780
tttgatgaag accattttct ggttctgtgt cctctgcctg ggctctggaa gaggccttcc    6840
cgtggccatt tctgtggagg gagggcagct ggccccagc cctgggggat tcctgagctg    6900
gcctgtctgc gtgggttttt gtatccagag ctgtttggat acagctgctt tgagctacag    6960
gacaaaggct gacagactca ctgggaagct cccaccccac tcaggggacc ccactcccct    7020
cacacacccc cccccacaag gaaccctcag gccaccctcc acgaggtgtg actaactatg    7080
caataatcca cccccaggtg cagccccagg gcctgcggag gcggtggcag actagagtct    7140
gagatgcccc gagcccaggc agctatttca gcctcctgtt tggtggggtg gcacctgttt    7200
cccgggcaat ttaacaatgt ctgaaaaggg actgtgagta atggctgtca cttgtcgggg    7260
gcccaagtgg ggtgctctgg tctgaccgat gtgtctccca gaactattct gggggcccga    7320
caggtgggcc tgggaggaag atgtttacat ttttaaaggt acactggtat ttatatttca    7380
aacattttgt atcaaggaaa cgttttgtat agttatatgt acagtttatt gatattcaat    7440
aaagcagtta atttatatat taaaaagtct ttggtgtcat agaggagtgg gtattttgaa    7500
aggtctttgg taagggagga ggggacagga attcctgaag cttagatatt tctgacacag    7560
ccttaaatct tgtccttgga aacatcatag ggctttggag tcctgggtgt cactgtcagg    7620
gaccttatga gactgggttt tcccgttggc ctgggtgtcc tgtctgctgc tgtttgggtg    7680
agccagcggc atccatacga gctcttcact atacactgtg gcttttact ttctcgttct    7740 tgaattttga agttgatctg g                                               7761
```

<210> SEQ ID NO 2
<211> LENGTH: 1708
<212> TYPE: DNA
<213> ORGANISM: Homo sapiens
<220> FEATURE:
<221> NAME/KEY: misc_feature
<223> OTHER INFORMATION: This sequence is a combined DNA/RNA sequence

<400> SEQUENCE: 2

```
ggcacggcct agcgagtggt tcttctgcgc tactgctgcg cgaatcggcg accccagtgc      60
ctcgaccact atgccgcgct cttttcctcgt caggaagccc tccgacccca atcggaagcc    120
taactacagc gagctgcagg actctaatcc agagtttacc ttccagcagc cctacgacca    180
ggcccacctg ctggcagcca tcccacctcc ggagatcctc aaccccaccg cctcgctgcc    240
aatgctcatc tgggactctg tcctggcgcc ccaagcccag ccaattgcct gggcctccct    300
tcggctccag gagagtccca gggtggcaga gctgacctcc ctgtcagatg aggacagtgg    360
gaaaggctcc cagccccca gcccaccctc accggctcct tcgtccttct cctctacttc    420
agtctcttcc ttggaggccg aggcctatgc tgccttccca ggcttgggcc aagtgcccaa    480
gcagctggcc cagctctctg aggccaagga tctccaggct cgaaaggcct tcaactgcaa    540
atactgcaac aaggaatacc tcagcctggg tgccctcaag atgcacatcc gaagccacac    600
gctgccctgc gtctgcggaa cctgcgggaa ggccttctct aggccctggc tgctacaagg    660
ccatgtccgg acccacactg gcgagaagcc cttctcctgt ccccactgca gccgtgcctt    720
cgctgaccgc tccaacctgc gggcccacct ccagacccac tcagatgtca agaagtacca    780
gtgccaggcg tgtgctcgga ccttctcccg aatgtccctg ctccacaagc accaagagtc    840
cggctgctca ggatgtcccc gctgaccctc gaggctccct cttcctctcc ataccctgccc   900 ctgcctgaca gccttcccca gctccagcag gaaggacccc acatccttct cactgccatg    960
gaattccctc ctgagtgccc cacttctggc cacatcagcc ccacaggact tgatgaaga    1020
```

```
ccatttctg gttctgtgtc ctctgcctgg gctctggaag aggccttccc atggccattt    1080
ctgtggaggg agggcagctg gcccccagcc ctgggggatt cctgagctgg cctgtctgcg    1140 tgggttttg tatccagagc tgtttggata cagctgcttt gagctacagg acaaaggctg    1200
acagactcac tgggaagctc ccaccccact caggggaccc cactcccctc acacacaccc    1260
ccccacaagg aaccctcagg ccaccctcca cgaggtgtga ctaactatgc aataatccac    1320
ccccaggtgc agccccaggg cctgcggagg cggtggcaga ctagagtctg agatgccccg    1380
agcccaggca gctatttcag cctcctgttt ggtggggtgg cacctgtttc ccggcaatt    1440 taacaatgtc tgaaaaggga ctgtgagtaa tggctgtcac ttgtcggggg cccaagtggg    1500
gtgctctggt ctgaccgatg tgtctcccag aactattctg ggggcccgac aggtgggcct    1560
gggaggaaga tgtttacatt tttaaaggta cactggtatt tatatttcaa acattttgta    1620
tcaaggaaac gttttgtata gttatatgta cagtttattg atattcaata aagcagttaa    1680
tttatatatt aaaaaaaaaa aaaaaaaa                                      1708
```

<210> SEQ ID NO 3
<211> LENGTH: 264
<212> TYPE: PRT
<213> ORGANISM: human

<400> SEQUENCE: 3

```
Met Pro Arg Ser Phe Leu Val Arg Lys Pro Ser Asp Pro Asn Arg Lys
1               5                   10                  15

Pro Asn Tyr Ser Glu Leu Gln Asp Ser Asn Pro Glu Phe Thr Phe Gln
            20                  25                  30

Gln Pro Tyr Asp Gln Ala His Leu Leu Ala Ala Ile Pro Pro Pro Glu
        35                  40                  45

Ile Leu Asn Pro Thr Ala Ser Leu Pro Met Leu Ile Trp Asp Ser Val
    50                  55                  60

Leu Ala Pro Gln Ala Gln Pro Ile Ala Trp Ala Ser Leu Arg Leu Gln
65                  70                  75                  80

Glu Ser Pro Arg Val Ala Glu Leu Thr Ser Leu Ser Asp Glu Asp Ser
                85                  90                  95

Gly Lys Gly Ser Gln Pro Pro Ser Pro Pro Ser Pro Ala Pro Ser Ser
            100                 105                 110

Phe Ser Ser Thr Ser Val Ser Ser Leu Glu Ala Glu Ala Tyr Ala Ala
        115                 120                 125

Phe Pro Gly Leu Gly Gln Val Pro Lys Gln Leu Ala Gln Leu Ser Glu
    130                 135                 140

Ala Lys Asp Leu Gln Ala Arg Lys Ala Phe Asn Cys Lys Tyr Cys Asn
145                 150                 155                 160

Lys Glu Tyr Leu Ser Leu Gly Ala Leu Lys Met His Ile Arg Ser His
                165                 170                 175

Thr Leu Pro Cys Val Cys Gly Thr Cys Gly Lys Ala Phe Ser Arg Pro
            180                 185                 190

Trp Leu Leu Gln Gly His Val Arg Thr His Thr Gly Glu Lys Pro Phe
        195                 200                 205

Ser Cys Pro His Cys Ser Arg Ala Phe Ala Asp Arg Ser Asn Leu Arg
    210                 215                 220

Ala His Leu Gln Thr His Ser Asp Val Lys Lys Tyr Gln Cys Gln Ala
225                 230                 235                 240

Cys Ala Arg Thr Phe Ser Arg Met Ser Leu Leu His Lys His Gln Glu
                245                 250                 255
```

Ser Gly Cys Ser Gly Cys Pro Arg
            260

<210> SEQ ID NO 4
<211> LENGTH: 1613
<212> TYPE: DNA
<213> ORGANISM: murine
<220> FEATURE:
<221> NAME/KEY: misc_feature
<222> LOCATION: (1)...(1613)
<223> OTHER INFORMATION: This sequence is a combined DNA/RNA sequence

<400> SEQUENCE: 4
cggagttgac taccgacctt gcgcgacccg gtgaccccga ctacctaggt cgctctggcc      60
aacatgccgc gctccttcct ggtcaggaag ccgtccgacc ccgccggaa gcccaactat      120
agcgagctgc aggacgcgtg tgtggagttc accttccagc agccctacga ccaggcccac    180
ctgctggccg ccatccctcc gcccgaggtc ctcaaccccg ccgcttcgct gcccacccct    240
atctgggact ctctcctggt accccaagtg cggccggttg cctgggccac cctcccgctg    300
cgggagagcc ccaaggccgt agagctgacc tcgctgtccg atgaggacag tggcaaaagc    360
tcccagccgc ccagcccgcc ctcgccggcg ccgtcgtcct tctcgtccac ctcggcctcg    420
tccctggagg ccgaggcctt catcgccttc cctggcttgg ccaacttcc caagcagctg    480
gccaggctct cggtggccaa ggaccccag tcgcggaaga tcttcaactg caaatattgt    540
aacaaggagt acctcagcct gggcgctctg aagatgcaca tccgaagcca cacgctgcct    600
tgtgtctgca cgacctgtgg aaaggccttc tctaggccct ggctgcttca gggccacgtc    660
cgcacccaca ctggtgagaa gccattctcc tgctcccact gcaaccgtgc ttttgctgac    720
cgctccaacc tgcgtgccca cctccaaacc cactcggatg tgaagagata ccagtgccag    780
gcctgtgccc gaaccttctc ccgcatgtcc ttgctccaca agcaccaaga gtctggctgc    840
tccggaggcc ctcgctgacc ctgctacctc cccatcctcg ctggcatctt cccggagctc    900
accctcctcc tcactgccag gactccttcc agccttggtc cggggacctg tggcgtccat    960
gtctggacct ggttcctgct tggctctctt ggtggccttt gccgcaggtg gctgatggag    1020
tgcctttgta cccgcccaga gcctcctacc cctcagtatt catgaggtgt agcctctgga    1080
cacagctgct tcgagccata gaactaaagc caacccactg gctgggaagc ttgaaccccg    1140
ctcaggggac cccacttccc tacctccctc aaggacccttt caggccacct tctttgaggt    1200
acaacagact atgcaaatagt tccctcccc ccacccgt ccagctgtaa ccatgcctca    1260
gcagggtggt tactggacac atgtccaggt gccctgggc ctgggcaact gtttcagccc    1320
ccgcccccat ttgtcctggt gacacctgtt tcacagcagt ttaactgtct cagaagggac    1380
catgaataat ggccatcact tgttaggggc caagtggggt gcttcagcct ggccaatgtg    1440
tctcccagaa ctattttggg gcccaacagg tggccccggg agaaagatgt ttacatttta    1500
aaggtattta tattgtaagc agcatttgt atagttaata tgtacagttt attgatattc    1560
aataaaatgg ttaatttata tactaaaaaa aaaaaaaaaa aaaaaaaaaa aaa           1613

<210> SEQ ID NO 5
<211> LENGTH: 264
<212> TYPE: PRT
<213> ORGANISM: murine

<400> SEQUENCE: 5

Met Pro Arg Ser Phe Leu Val Arg Lys Pro Ser Asp Pro Arg Arg Lys
1               5                   10                  15

```
Pro Asn Tyr Ser Glu Leu Gln Asp Ala Cys Val Glu Phe Thr Phe Gln
            20                  25                  30

Gln Pro Tyr Asp Gln Ala His Leu Leu Ala Ala Ile Pro Pro Pro Glu
            35                  40                  45

Val Leu Asn Pro Ala Ala Ser Leu Pro Thr Leu Ile Trp Asp Ser Leu
 50                      55                  60

Leu Val Pro Gln Val Arg Pro Val Ala Trp Ala Thr Leu Pro Leu Arg
 65                  70                  75                  80

Glu Ser Pro Lys Ala Val Glu Leu Thr Ser Leu Ser Asp Glu Asp Ser
            85                  90                  95

Gly Lys Ser Ser Gln Pro Pro Ser Pro Pro Ser Pro Ala Pro Ser Ser
            100                 105                 110

Phe Ser Ser Thr Ser Ala Ser Ser Leu Glu Ala Glu Ala Phe Ile Ala
            115                 120                 125

Phe Pro Gly Leu Gly Gln Leu Pro Lys Gln Leu Ala Arg Leu Ser Val
            130                 135                 140

Ala Lys Asp Pro Gln Ser Arg Lys Ile Phe Asn Cys Lys Tyr Cys Asn
145                     150                 155                 160

Lys Glu Tyr Leu Ser Leu Gly Ala Leu Lys Met His Ile Arg Ser His
                165                 170                 175

Thr Leu Pro Cys Val Cys Thr Thr Cys Gly Lys Ala Phe Ser Arg Pro
            180                 185                 190

Trp Leu Leu Gln Gly His Val Arg Thr His Thr Gly Glu Lys Pro Phe
            195                 200                 205

Ser Cys Ser His Cys Asn Arg Ala Phe Ala Asp Arg Ser Asn Leu Arg
    210                 215                 220

Ala His Leu Gln Thr His Ser Asp Val Lys Arg Tyr Gln Cys Gln Ala
225                     230                 235                 240

Cys Ala Arg Thr Phe Ser Arg Met Ser Leu Leu His Lys His Gln Glu
            245                 250                 255

Ser Gly Cys Ser Gly Gly Pro Arg
            260
```

METHOD USING SNAIL TRANSCRIPTIONAL REPRESSOR

BACKGROUND OF THE INVENTION

Breast cancer is the most common malignancy diagnosed among women worldwide, and is the leading cause of cancer mortality (Parkin et al., *CA Cancer J. Clin.* 55:74-108 (2005)). In 2005, more than 1.1 million women will be diagnosed with breast cancer and over than 400,000 women will die from this disease (Parkin et al., supra (2005)). Moreover, breast cancer disproportionately affects young women, as highlighted by the fact that it represents the leading cause of death from disease among women ages 25-54. Fortunately, while breast cancer incidence has steadily increased in Western countries over the past 50 years, breast cancer mortality rates have declined for more than a decade, due to continued advances in early detection, surgery, radiation, and adjuvant therapy. Indeed, nearly 90% of women diagnosed with breast cancer will survive for at least 5 years.

As a consequence of its high incidence and favorable prognosis, the prevalence of breast cancer is extremely high. More than 4 million women are currently living with a diagnosis of breast cancer, making this the most prevalent cancer in the world today (American Cancer Society, *Breast Cancer Facts & Figures* 2003, Atlanta, Ga., pp. 1-27 (2003); National Cancer Institute, Cancer Control and Population Sciences, U.S. National Institutes of Health, (2004); Parkin et al., supra (2005)). Among these women, tumor dormancy followed by recurrence—either local, regional, or distant—represents the most common cause of breast cancer mortality. Even among those patients whose breast cancers have not spread to axillary lymph nodes by the time of surgery, 25-year recurrence rates have been reported at 43-53% (Fisher et al., *Lancet* 364:858-868 (2004)). This suggests that, in many cases, tumor cells have already disseminated to distant sites by the time that breast cancers are diagnosed. Indeed, analysis of bone marrow specimens indicates that residual cancer cells are detectable in up to 40% of primary breast cancer patients who do not have any clinical or histopathological signs of metastasis (Pantel et al., *Semin. Cancer Biol.* 11:327-337 (2001); Solakoglu et al., *Proc. Natl. Acad. Sci. U.S.A.* 99(4): 2246-51 (2002); Pantel et al., *Clin. Cancer Res.* 9(17):6326-34 (2003)). These residual neoplastic cells are capable of surviving multiple courses of chemotherapy, and persist in a latent state following the apparent cure of the tumor from which they arose (Thurm et al., *Clin. Cancer Res.* 9(7):2598-604 (2003)).

The peak hazard of recurrence for breast cancer in humans occurs in the interval between years 1 and 2 after surgery (Demicheli et al., *Breast Cancer Res.* 6:689-696 (2004); Retsky et al., *Breast Cancer Res. Treat.* 65:217-224 (2001); Saphner et al., *J. Clin. Oncol.* 14:2738-2746 (1996)). In fact, more than a quarter of all relapses in premenopausal, node-positive patients occur within the first 10 months following resection. Nevertheless, residual neoplastic cells may linger unrecognized for more than a decade before emerging as recurrent disease. Consequently, breast cancers that appear cured may resurface as local or distant tumor recurrences 10 or 20 years later (Fentiman et al., *Breast* 9:5-8 (2000); Fisher et al., supra (2004); Weiss et al., *J. Clin. Oncol.* 21:1825-1835 (2003)). These, and other observations, argue persuasively that breast cancer recurrence represents the single greatest obstacle to curing this disease.

Despite the central role that recurrence plays in breast cancer mortality, virtually nothing is known about the cellular or molecular events responsible for this ominous clinical event. To date, a limited number of clinical and molecular characteristics of breast cancers have been shown to correlate with relapse-free survival. In women with breast cancer, the most important factors for predicting recurrence are tumor size and the extent of lymph node involvement (Carter et al., *Cancer* 63:181-187 (1989); Valagussa et al., *Cancer* 41:1170-1178 (1978)). In addition to these clinical parameters, a number of molecular markers for aggressive tumor behavior can be used to identify breast cancer patients at high risk for recurrence, including HER2/neu expression, c-myc amplification, and estrogen receptor negativity (Coradini et al., *Curr. Opin. Obstet. Gynecol.* 16:49-55 (2004); Schlotter et al., *Breast Cancer Res.* 5:R30-36 (2003)). Expression of a recently-identified kinase, Hunk, has been identified as a biomarker of metastasis-free survival (U.S. patent application Ser. No. 10/032,256, filed Dec. 21, 2001 and U.S. provisional patent application No. 60/671,655, filed Apr. 15, 2005). However, none of these, or any other molecular prognostic markers, have been shown to play a causal role in breast cancer recurrence. As such, their mechanistic relationship to this process is purely speculative.

Given the large number of women currently living with a diagnosis of breast cancer, elucidating the molecular mechanisms that allow tumors to evade primary therapy and recur is a critical goal of breast cancer research. In particular, understanding the biology of tumor latency, as well as the events that lead to recurrence would permit improvements in the prediction, prevention, and treatment of breast cancer recurrence. Achieving this goal, however, has been hampered by the lack of animal models that faithfully recapitulate these fundamental steps of breast cancer progression. Such models are essential for the rational development and testing of therapeutics targeted against the residual population of neoplastic cells that is responsible for the majority of breast cancer deaths.

Further compounding difficulties in understanding breast cancer recurrence is the limited availability of clinical material for analysis. While molecular profiles for primary human breast cancers have become widely available, no comprehensive molecular analysis of recurrent human breast cancers currently exists. Consequently, not only is information lacking regarding pathways causally involved in recurrence, but also lacking is even a rudimentary understanding of the specific molecular features that distinguish recurrent breast cancers from the primary tumors from which they arose.

One molecular prognostic marker for poor clinical outcome in breast cancer patients is the proto-oncogene, HER2/neu. Amplification and overexpression of this receptor tyrosine kinase occurs in 15-30% of primary human breast cancers and is associated with aggressive tumor behavior, high rates of relapse, and poor prognosis (Berger et al., *Cancer Res.* 48:1238-1243 (1988); Slamon et al., *Science* 235: 177-182 (1987)). In recent years, Trastuzumab (Herceptin®), a neutralizing antibody that inhibits the activity of HER2/neu, has been tested in clinical trials for patients with HER2/neu-amplified breast cancers. The efficacy of this agent in slowing disease progression and prolonging survival, even in advanced stages of disease, has been demonstrated in multiple studies (Baselga et al., *J. Clin. Oncol.* 14:737-744 (1996); Cobleigh et al., *J Clin Oncol.* 17:2639-2648 (1999); Slamon et al., *N. Engl. J. Med.* 344:783-792 (2001); Vogel et al., *J. Clin. Oncol.* 20:719-726 (2002); Wang et al., *Semin. Oncol.* 28:115-124 (2001); Wang et al., *Semin. Oncol.* 28:21-29 (2001)). However, even in cases in which Trastuzumab is combined with standard chemotherapeutic regimens, breast cancers often eventually become resistant to therapy and recur (Hortobagyi et al., *Semin. Oncol.* 28:43-47 (2001)). As with cancer recurrence in general, however, the mechanisms by which HER2/neu-amplified breast tumor cells evade the blockade of this pathway are poorly understood.

In light of these findings, it is clear that prior to the present invention, there was an unmet need in the art to study the cellular and molecular events involved in breast cancer recurrence, and to develop a method for assessing the risk of breast cancer recurrence based on a molecular prognostic marker that is independent of known prognostic markers and is likely to play a causal role in recurrence.

SUMMARY OF THE INVENTION

The present invention relates generally to a prognostic molecular marker for breast cancer recurrence, demonstrates its causal role in recurrence, and provides methods of use thereof. Specifically, the expression of Snail, a zinc finger transcriptional repressor, is correlated to the risk of breast cancer recurrence, and to the likelihood of recurrence-free survival in subjects diagnosed with breast cancer. In one embodiment, a method is provided for assessing breast cancer recurrence based on the expression of human Snail in a tumor sample from a subject diagnosed with breast cancer. The invention further provides methods of identifying potential therapeutics for treatment of breast cancer characterized by high expression of Snail and methods of reducing Snail expression, useful in therapeutic applications, as well as research applications. In yet another embodiment, a method of reducing the risk of breast cancer recurrence in a subject diagnosed with breast cancer is provided. In another embodiment, a kit is provided for measuring the expression of Snail.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended figures, which are not intended to be limiting.

FIG. 1A depicts the recurrence-free survival curve for uninduced MTB/TAN mice (n=13) and MTB/TAN mice de-induced after the development of primary tumors while drinking 2 mg/ml doxycycline (n=62). FIG. 1B depicts a growth chart showing the timing of recurrent neu-induced tumor growth. Tumor volumes were measured following doxycycline withdrawal. Time zero=day on which doxycycline was withdrawn from mice bearing established tumors; and is indicated by an arrow. A bracket indicates the range of times (relative to doxycycline withdrawal) at which neu was initially induced via doxycycline administration. FIG. 1C depicts luciferase imaging of MTB/TAN mice with primary tumors, fully regressed tumors, and a recurrent tumor, demonstrating that recurrent tumors do not express the TAN transgene in the absence of doxycycline. A mouse with primary tumors at the following locations is shown with (FIG. 1C, panel B) and without (FIG. 1C, panel A) luciferase overlay: 1L—6×6 mm$^2$, 2L—3×3 mm$^2$, 3LA—12×14 mm$^2$, 3LB—6×6 mm$^2$, 5L—3×3 mm$^2$, 1R—2×2 mm$^2$, 2R—2×2 mm$^2$, 3R—3×3 mm$^2$, 4R—2×2 mm$^2$. The indicators, 1L, 2L, etc., indicate in which of the five mouse mammary glands the tumor is located and on what side of the mouse, e.g., "1L" indicates that the tumor is in the first mammary gland, on the left side of the mouse. Arrows indicate the sites of all but the 2R tumor. The same mouse after full regression of tumors is shown with luciferase overlay in panel C. Note the absence of any visible masses or luciferase activity. A second mouse with a recurrent tumor in mammary gland 3R (arrow) is shown in panel D, also absent luciferase activity.

FIG. 2A shows the change from epithelial morphology and high levels of CK8 expression in primary tumors to the spindle cell morphology and undetectable CK8 expression in recurrent tumors. Magnification 400×. FIG. 2B depicts a Northern analysis of primary and recurrent MTB/TAN tumors for expression of NeuNT, E-cadherin, Vimentin, and Fibronectin. Northern probes were generated using cDNA fragments corresponding to the following sequences: NeuNT: nt 3530 Neu-112 IRES; mE-cadherin: nt 3276-3646; hVimentin: nt 52-878; mFibronectin: nt 283-708. 18S rRNA is shown as a loading control. FIG. 2C depicts immunofluorescence analysis of representative primary and recurrent tumors demonstrating Cytokeratin 8, E-cadherin, and S100A4 expression. Magnification 400×.

FIGS. 3A and 3C show primary tumor grafts allowed to grow out on doxycycline, and then biopsied prior to the withdrawal of doxycycline. FIGS. 3B and 3D show tumor either partially regressed and then resumed growth in the absence of doxycycline (FIG. 3B) or completely regressed and recurred at the same site (FIG. 3D). Note that the tumors growing in the absence of doxycycline display spindle cell morphology, while the corresponding primary tumor grafts from which they arose display cuboidal, epithelial cell morphology. Magnification 400×.

FIG. 4A depicts bar graphs demonstrating average Snail and Slug expression levels in primary and recurrent tumors, as determined by Affymetrix® oligonucleotide microarray analysis. Expression levels were significantly different between primary tumors and recurrent tumors for both genes, as designated by asterisks (p=0.000008 for Snail, p=0.0001 for Slug). FIG. 4B depicts a Northern analysis of Snail expression in primary, recurrent, and incompletely regressing ("Inc. Reg.") tumors. Snail northern probe corresponds to nucleotides 700-1066 of the mouse Snail cDNA sequence. 18S rRNA is shown as a loading control.

FIG. 5A depicts a Western analysis of Snail expression in pk1 and pk1-Snail infected primary tumor cells. B-tubulin is shown as a loading control. FIG. 5B are photomicrographs of pk1 and pk1-Snail infected primary tumor cells, taken after 13 days of puromycin selection, and showing the spindle cell morphology of the pk1-Snail infected cells. Magnification 400×. FIG. 5C depicts images of immunofluorescence studies of an uninfected primary tumor cell line, an uninfected recurrent tumor cell line, the same primary tumor cell line infected with pk1, and the same primary tumor cell line infected with pk1-Snail. Cells are stained for the epithelial cell markers, Cytokeratin 8 and E-cadherin, as well as for the mesenchymal markers, S100A4 and Fibronectin. Magnification 400×.

FIG. 6A are images of hematoxylin and eosin stained sections of tumors formed by pk1- and pk1-Snail-infected tumor cells, harvested from mice on doxycycline, and of doxycycline-independent pk1-Snail recurrent tumors. Magnification 400×. FIG. 6B depicts luciferase activity levels in pk1 and pk1-Snail tumors arising on doxycycline, and in pk1-Snail recurrent tumors (Rec) arising after the withdrawal of doxycycline. Averages and standard deviations, respectively, are as follows: Pk1 17,400,000 and 4,200,000; pk1-Snail 13,600,000 and 6,400,000; pk1-Snail recurrence 4540 and 7880. N=6 for each tumor type. FIG. 6C is a recurrence-free survival curve for pk1-infected and pk1-Snail-infected primary tumor cells. Mice were removed from doxycycline on day 0, after the injected tumor cells had formed a tumor 9 mm$^3$ in size. Recurrence rates are significantly higher in pk1-Snail-infected cells, with a p-value<0.0001. FIG. 6D are images of immunofluorescence studies of tumors formed by pk1- and pk1-Snail-infected tumor cells, harvested from mice on doxycycline, and of doxycycline-independent pk1-Snail recurrent tumors. Tumors were stained for Cytokeratin 8, E-cadherin, and S100A4. Note the loss of E-cadherin expression and the induction of S100A4 expression in pk1-Snail primary and recurrent tumors. Magnification 400×.

FIG. 7A depicts the five-year recurrence-free survival (RFS) based on low vs. high Snail expression in a microarray analysis set of locally advanced human breast cancer samples published by Sorlie et al. (*Proc. Natl. Acad. Sci. USA* 100: 8418-8423 (2003)). FIG. 7B depicts the five-year recurrence-free survival (RFS) based on low vs. high Snail expression in a microarray analysis set of lymph node negative human breast cancer samples published by van't Veer et al. (*Nature.* 415:530-536 (2002)). FIG. 7C depicts the five-year recurrence-free survival (RFS) based on low vs. high Snail expression in a microarray analysis set of lymph-node negative, ER positive and ER negative human breast cancer samples published by Wang et al. (*Lancet* 365:671-679 (2005)). FIG. 7D depicts the five-year recurrence-free survival (RFS) based on low vs. high Snail expression in a microarray analysis set of hormone receptor-positive human breast cancer samples published by Ma et al. (*Cancer Cell.* 5:607-616 (2004)).

DETAILED DESCRIPTION OF CERTAIN PREFERRED EMBODIMENTS

Figures 1A, 1B, 1C:
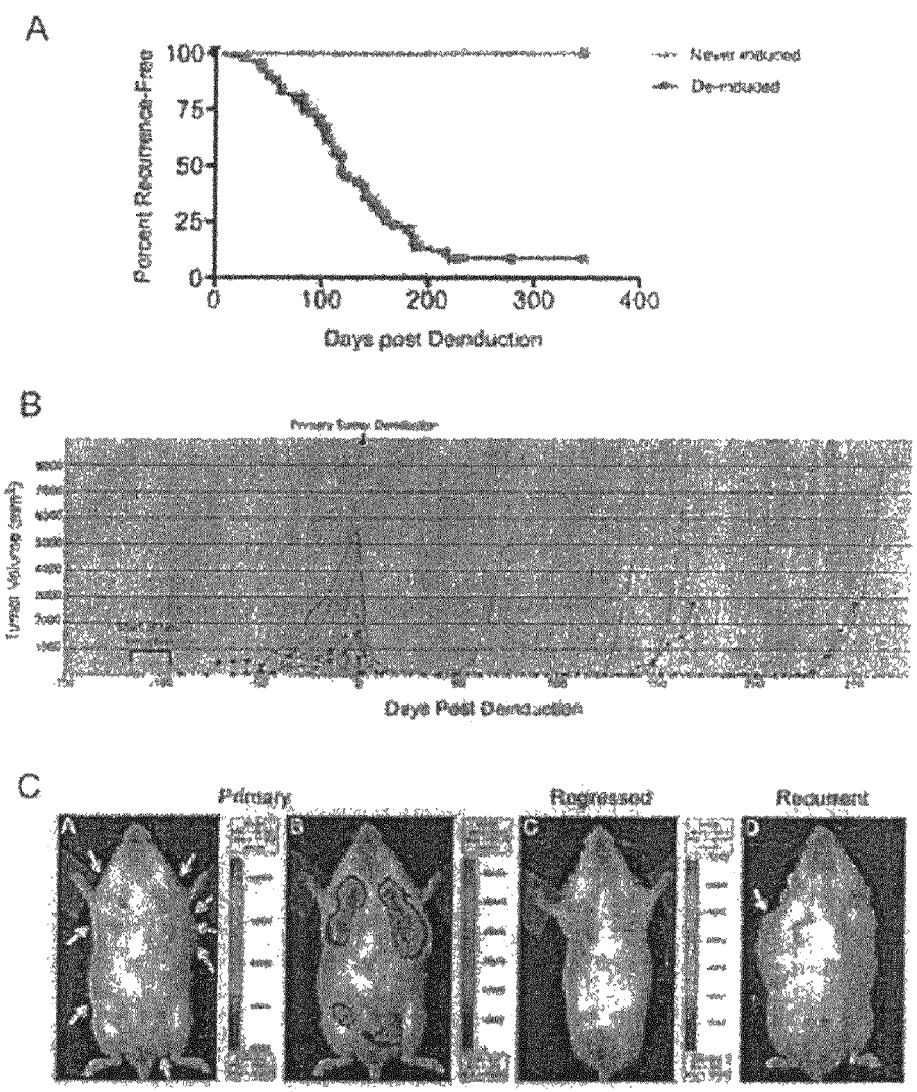
FIGS. 1A through 1C depict that uninduced MTB/TAN animals do not develop tumors, even over periods exceeding 18 months, and that recurrent tumors always appear at a site at which a primary tumor had previously existed.

The present invention identifies Snail as a molecular prognostic marker for breast cancer recurrence, demonstrates its causal role in recurrence, and provides methods for its use. As described in greater detail below, embodiments of the invention address methods for assessing breast cancer recurrence based on the expression of human gene Snail in a tumor sample from a subject diagnosed with breast cancer, for assessing the likelihood of recurrence-free survival of a subject diagnosed with breast cancer, and for reducing the risk of breast cancer recurrence in a subject diagnosed with breast cancer is provided. Important to these methods is the identification of potentially therapeutic compounds for breast cancer treatment, as well as kits for measuring the expression of Snail.

The prognostic and therapeutic methods and compositions of the invention may be used with any subject that is a mammal. The mammal is preferably a veterinary animal, including a primate, and more preferably, a human. The prognostic methods are especially advantageous for identifying subjects at an elevated risk of recurrence and who might, therefore, benefit from more frequent disease monitoring and/or prophylactic or additional treatment.

Given the importance of the proto-oncogene HER2/neu in human breast cancers and the recent development of treatments that directly target this oncogenic pathway, the experiments described herein used a mammary-specific, conditional transgenic model to investigate the effects of neu withdrawal on the regression and recurrence of mammary tumors induced by this oncogene (D'Cruz et al., *Nat. Med.* 7:235-239 (2001); Gu et al., *Nature.* 387:819-823 (1997); Gunther et al., *Faseb J.* 16:283-292 (2002); Moody et al., *Cancer Cell* 2:451-461 (2002)). Such a model permits the analysis of tumor growth, treatment, and recurrence within the context of the molecular targeting of a dominant oncogenic pathway in an intact tumor. Thus, the present invention used the tetracycline-regulatory system to express inducibly an activated form of neu in the mammary epithelium of transgenic mice (Moody et al., supra, (2002)). When treated with doxycycline, these mice develop multiple, invasive, mammary adenocarcinomas that regress to a non-palpable state upon targeted down-regulation of the neu pathway. However, consistent with the behavior of human malignancies, the vast majority of mice harboring fully regressed tumors ultimately developed recurrences in the absence of doxycycline treatment and neu expression. As such, this model recapitulates key features of the natural history of human breast cancers that are relevant to tumor recurrence.

The unique properties of this conditional transgenic mouse model permitted the elucidation of secondary pathways involved in breast cancer progression and escape. As described in the Examples below, using this model, identification was made of a molecular pathway involved in spontaneous mammary cancer recurrence. Presented herein is the first in vivo evidence for a molecular mechanism that contributes to mammary tumor recurrence, as well as one of the first models for spontaneous tumor recurrence in intact animals. These data demonstrate that recurrent neu-induced mammary tumors display phenotypic and molecular alterations characteristic of cells that have undergone EMT and Snail expression is spontaneously up-regulated during the process of tumor recurrence as it occurs in intact animals, and that the process of recurrence is accompanied by epithelial-to-mesenchymal transition ("EMT"). EMT is an cellular transition in which Snail has been implicated and has been linked to breast cancer progression. Consistent with a causal role for Snail in EMT and breast cancer progression, the present invention further shows that: 1) Snail is sufficient to induce EMT in neu-induced primary tumor cells; 2) Snail promotes rapid mammary tumor recurrence in vivo following down-regulation of the neu pathway; and 3) high levels of Snail expression strongly predict decreased recurrence-free survival in women with breast cancer in a wide variety of clinical contexts and is largely independent of currently recognized molecular and cellular prognostic markers.

Moreover, the ability of Snail to predict recurrence-free survival in women is not due to its preferential expression within any currently recognized aggressive subtype of breast cancer. That is, if Snail's role in tumor recurrence were restricted to HER2/neu-amplified breast cancers in humans, it would not be expected to observe the general relationship between Snail expression and breast cancer recurrence, since HER2/neu-amplified tumors represent only a small proportion of the cancers in the data sets examined. To the contrary, however, consistent with a more general role for Snail in human breast cancer recurrence, the present invention further demonstrates that Snail is not preferentially expressed in HER2/neu-amplified tumors or in other breast cancer subtypes. Since a significant association between Snail expression and the likelihood of recurrence was observed for both ER-positive and ER-negative breast cancers, HER2/neu-amplified and unamplified breast cancers, and breast cancers with and without lymphatic spread, these data indicate that Snail appears to be linked to breast cancer recurrence in a wide variety of clinical contexts.

Figure 4A:
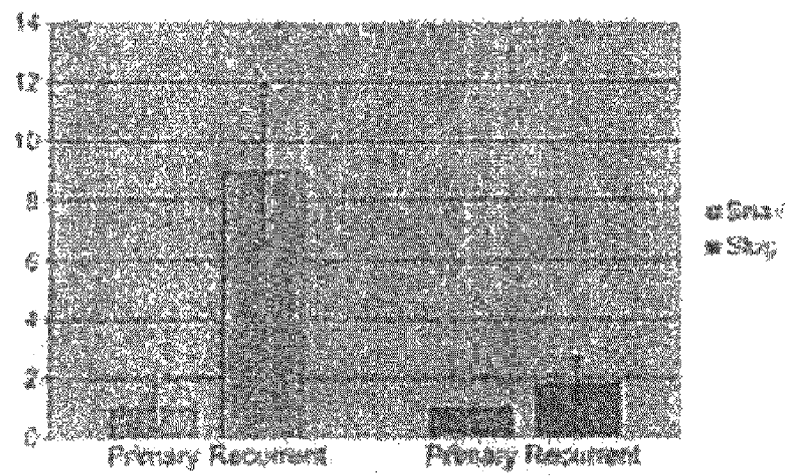
FIGS. 4A and 4B show that recurrent tumors express increased levels of Snail as compared to primary tumors.
Figure 4B:
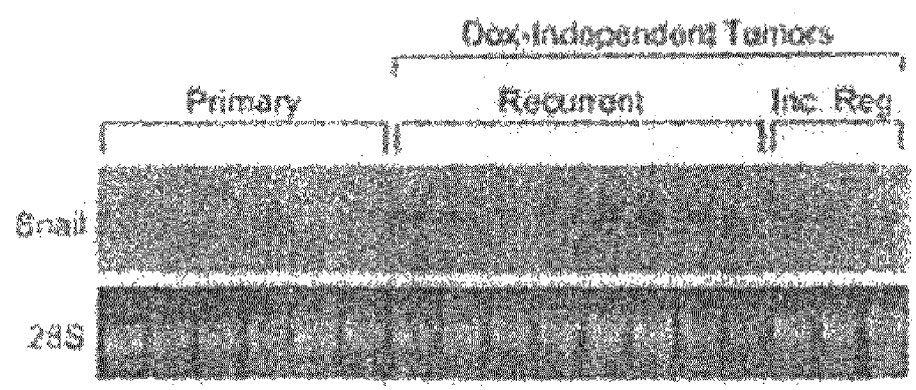

Importantly, the significant correlation that was detected between Snail expression and disease recurrence in humans was observed in primary tumors, implying that Snail activation within primary tumors plays a role in promoting tumor recurrence. Indeed, the present invention demonstrates that enforced Snail up-regulation in murine primary tumors is sufficient to dramatically promote tumor recurrence. Moreover, in the subset of primary neu-induced tumors that did not regress fully when Neu was down-regulated (i.e., had progressed to a neu-independent state), high levels of Snail expression were identified that were comparable to those found in recurrent tumors (FIG. 4B). Moreover, notably, the association between Snail expression in primary human tumors and breast cancer recurrence that was observed is not inconsistent with the finding that spontaneous Snail up-regulation in the mouse more typically occurs in recurrent tumors. In aggregate, these observations provide strong evidence that Snail plays a role in breast cancer recurrence.

Snail expression has previously been correlated with histological grade and lymph node metastasis in a panel of 17 human breast cancers (Blanco et al., *Oncogene* 21:3241-3246 (2002)). While a significant correlation between Snail expression and histological grade was detected in one breast cancer data set by one method of analysis, consistent correlations between Snail expression and histological grade across most data sets have not previously been found, nor have correlations been made between Snail expression and lymph node status in any of the data sets examined. In light of that finding, four independent microarray expression data sets derived from prospectively harvested human breast cancer samples were analyzed, and revealed that high levels of Snail expression strongly predict decreased recurrence-free survival in women with breast cancer. Moreover, the findings confirmed that the prognostic value of Snail expression operates independently of currently used prognostic indicators for breast cancer. Thus, the present invention presents, for the first time, a demonstrated molecular pathway involved in mammary tumor recurrence in vivo and indicate that Snail plays a role in the progression of human breast cancers. As such, while in larger, more diverse tumor sets, Snail expression levels may not correlate significantly with tumor grade or lymph node status, it remains a significant predictor of recurrence-free survival.

Therefore, since as noted Snail expression does not consistently correlate with tumor size, HER2 status, ER status, ductal versus lobular subtype, or luminal versus basal subtype, its prognostic significance is comparable to other currently used prognostic markers. This indicates that the association between Snail levels and recurrence-free survival is not simply due to its selective expression in a presently recognized subset of aggressive breast cancers. Thus, independent of each of the most commonly used prognostic indicators, high Snail expression identifies a subset of human breast cancer patients at high risk for recurrence. Moreover, the hazard ratio associated with increased Snail expression is comparable to that observed for ER status, which represents one of the most commonly used clinical prognostic variables, as well as the most commonly-used target for breast cancer prevention and treatment.

While not wishing to be bound by theory, it is noted that the findings provided by the present invention directly address local recurrence. Local recurrence is a common sequela in breast cancer patients and is, in and of itself, a critical problem to understand. Local recurrence typically comprises up to one-third of all recurrences (Doyle et al., *Int. J. Radiat. Oncol. Biol. Phys.* 51:74-80 (2001); Fisher et al., *Lancet* 338:327-331 (1991); Fortin et al., *J. Clin. Oncol.* 17:101-109 (1999); Schmoor et al., *J. Clin. Oncol.* 18:1696-1708 (2000); Veronesi et al., *J. Natl. Cancer Inst.* 87:19-27 (1995)). Isolated local recurrence following breast conservation surgery with radiation treatment occurs in ~10-20% of women at 10 years. Considering that two thirds of the more than 200,000 women with breast cancer each year in the United States are treated with breast-conserving approaches, the magnitude of the problem of local recurrence is substantial.

There are several reasons to believe that this invention is also relevant to distant, as well as, local recurrence. For example, a priori considerations alone suggest that the processes by which tumor cells—whether local or distant—survive in a latent state and ultimately re-establish malignant growth are likely to be related mechanistically. Multiple studies have demonstrated that local recurrence is itself strongly associated with an increased risk both of distant recurrence (relative risk=5.1) and mortality (relative risk=3.6) (Doyle et al., supra (2001); Fisher et al., supra (1991); Fortin et al., supra (1999); Schmoor et al., supra (2000); Veronesi et al., supra (1995)). Thus, local recurrence strongly predicts distant recurrence. Moreover, even the timing of local recurrences after surgery is remarkably similar to that of distant recurrences (Demicheli et al., supra (2004); Retsky et al., supra (2001); Retsky et al., *Breast Cancer Res.* 7:37-40 (2005)). Together, these observations suggest that local and distant recurrence may result from similar processes. In other words, while local recurrence is essential to understand in and of itself, the associations between local recurrence and distant recurrence suggest that the mechanisms responsible for one may be informative for the other. As such, the findings herein that Snail expression predicts increased rates of both local and distant recurrence in humans and promotes local recurrence in mice, and raises the possibility that Snail may contribute to both processes.

Similarities between local and distant recurrences notwithstanding, distinctions between the processes of recurrence and metastasis must be considered since the mechanisms that allow latent tumor cells to survive and ultimately re-establish malignant growth are likely to differ from those that permit actively growing tumor cells to invade and spread to distant sites. While metastasis is a sine qua non of distant spread, it is clearly not required for local recurrence. Moreover, even in the case of distant recurrence, the mechanisms that permit metastatic cells to remain in a quiescent state and re-emerge at a later time are not the same as those that permit distant spread in the first place. Thus, the processes of recurrence and metastasis likely share a number of similar features, and distinct mechanisms almost certainly contribute to each process. It is, therefore, essential to distinguish these processes experimentally to permit elucidation of these separate mechanisms.

Snail Genes and Snail Proteins

As used herein, "Snail" refers to the protein product of a "Snail" gene. Specifically, when written in a non-italicized font, Snail refers to the protein, while the italicized term, Snail, refers to the gene encoding the protein. Thus, Snail refers to a nucleotide sequence that encodes a polypeptide having Snail activity. The genomic sequence of the human Snail gene is provided in SEQ ID NO. 1 (Paznekas et al.,

*Genomics* 62:42-49 (1999)). Characterization of the human Snail promoter has been performed by Barbera et al. (*Oncogene* 23:7345-7354 (2004)). The coding sequence is provided in SEQ ID NO. 2 (Accession No: NM_005985), and the amino acid sequence is provided in SEQ ID NO. 3. The coding sequence of the murine Snail gene is provided in SEQ ID NO. 4 and the deduced amino acid sequence is provided in SEQ ID NO. 5. In one embodiment, the Snail coding sequence has, at least, about 40% homology, or at least about 45%, 50%, 55%, 60%, 65%, 70%, 75%, 80%, or 85% homology, preferably at least about 90% homology, and more preferably, at least, about 95% homology to SEQ ID NO. 2 and encodes a polypeptide having Snail activity. Preferably, the Snail coding sequence is SEQ ID NO. 2.

As used herein, "homology" is used synonymously with "identity." "Homologous," as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 50% homology.

The determination of percent identity between two nucleotide or amino acid sequences may be accomplished using a mathematical algorithm. For example, a mathematical algorithm useful for comparing two sequences is the algorithm of Karlin and Altschul (*Proc. Natl. Acad. Sci. USA* 87:2264-2268 (1990)), modified as in Karlin and Altschul (*Proc. Natl. Acad. Sci. USA* 90:5873-5877 (1993)). This algorithm is incorporated into the NBLAST and XBLAST programs of Altschul et al. (*J. Mol. Biol.* 215:403-410 (1990)), and may be accessed, for example, at the National Center for Biotechnology Information (NCBI) world wide web site having the universal resource locator www(dot)ncbi(dot)nlm(dot)nih (dot)gov/BLAST/. BLAST nucleotide searches may be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches may be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST may be utilized as described in Altschul et al. (*Nucleic Acids Res.* 25:3389-3402 (1997)). Alternatively, PSI-Blast or PHI-Blast may be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) may be used. See www(dot)ncbi(dot)nlm (dot)nih(dot)gov.

The percent identity between two sequences may be determined using techniques similar to those described above, with or without allowing gaps. In calculating percent identity, typically exact matches are counted.

In another embodiment, the Snail sequence refers to a sequence that hybridizes to SEQ ID NO. 2 under stringent hybridization conditions, and that encodes a polypeptide having Snail activity. As used herein, "stringent hybridization conditions" refers to conditions for hybridization and washing under which nucleotide sequences typically remain hybridized to each other. Such stringent conditions are known to those skilled in the art and may be found, for instance, in Ausubel et al. (*Current Protocols in Molecular Biology*, John Wiley & Sons, New York (1997)). A preferred example of stringent hybridization conditions is hybridization in 6× sodium chloride/sodium citrate (SSC) at about 45° C., followed by one or more washes in 0.2×SSC, 0.1% SDS at 50° C. Washes may be performed at higher temperatures, such as, but not limited to 55° C., 60° C. and 65° C. Preferably, an isolated nucleotide that hybridizes under stringent conditions to SEQ ID NO. 2 corresponds to a naturally-occurring nucleotide. As used herein, a "naturally-occurring nucleotide" refers to an RNA or DNA molecule having a nucleotide sequence that occurs in nature (i.e. encodes a natural protein).

"Snail," "Snail polypeptide" and "Snail protein," used interchangeably herein, refer to polymeric sequence of amino acids that has Snail activity. In one embodiment, the Snail sequence has at least about 40% homology, or at least, about 45%, 50%, 55%, 60%, 65%, 70%, 75%, 80%, or 85% homology, preferably at least about 90% homology or at least about 95% homology to SEQ ID NO. 3, and in each case has Snail activity. Preferably, the Snail sequence is SEQ ID NO: 3.

Snail is a zinc finger protein ("ZFP") (reviewed in De Craene et al., *Cell Signal* 17:535-547 (2005)). ZFPs are proteins that bind to DNA in a sequence-specific manner. Zinc fingers were first identified in the transcription factor TFIIIA from the oocytes of the African clawed toad, *Xenopus laevis* and are widespread among eukaryotic cells. An exemplary motif characterizing one class of these proteins ($C_2H_2$ class) is -Cys-$(X)_{2-4}$-Cys-$(X)_{12}$-His-$(X)_{3-5}$-His (where X is any amino acid). A single finger domain is about 30 amino acids in length and several structural studies have demonstrated that it contains an alpha helix containing the two invariant histidine residues co-ordinated through zinc with the two cysteines of a single beta turn. Over 10,000 zinc finger sequences have been identified in several thousand known or putative transcription factors. ZFPs are involved not only in DNA-recognition, but also in RNA binding and protein-protein binding. See, e.g., Berg & Shi, *Science* 271:1081-1085 (1996). Human Snail has four zinc fingers in the C-terminal and an N-terminal SNAG domain (Katoh and Katoh, *Int. J. Mol. Med.* 11, 383-388 (2003)). In murine Snail, the SNAG domain recruits histone deacetylase 1 and 2 (HDAC1 and HDAC2) and co-repressor mSin3A to repress E-cadherin expression (Peinado et al., *Mol. Cell. Biol.* 24:306-319 (2004)).

A zinc finger recognition helix has four amino acid positions (−1, 2, 3 and 6) that typically direct DNA binding specificity. Amino acid changes at these positions typically reduce DNA binding affinity or may alter recognition specificity. Amino acids that are involved in the proper folding and hydrophobic core of a protein may generally tolerate conservative amino acid changes. Amino acids that are on the surface of a protein are typically the most tolerant of amino acid changes, with regard to folding and structure. There is extensive literature regarding specific zinc finger structure-function relationships, with regard both to proper folding of zinc fingers, as well as DNA binding activity, and this literature is known to the skilled artisan. Therefore, such a practitioner has extensive guidance regarding what amino acid changes at what positions in a Snail protein are likely to be tolerated in terms of the zinc finger structure and its function.

Conservative amino acid substitutions are recognized in the art, and modified Snail proteins may also be used in the methods of the present invention. Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

As used herein, "Snail activity" refers to Snail binding to a Snail "target molecule" with approximately the same affinity as binding by wild-type Snail under the same or similar conditions. By "target molecule" is meant a molecule with which a Snail protein binds or interacts in nature, and encompasses cognate DNA binding sites, cognate RNA binding sites and proteins, including, but not limited to, other transcriptional regulation proteins. An intended Snail target molecule is a Snail cognate DNA binding site. Snail activity may also include Snail repression of transcription. As used herein "approximately the same affinity" refers to a binding affinity that is not altered (reduced or increased) by more than about an order of magnitude. A Snail cognate binding site has a 6 nucleotide sequence, 5'-CAGGTG-3' referred to as an E-box. Exemplary DNA binding sites for Snail are located, for instance, in the promoter regions of genes that are repressed by Snail, including, but not limited to, E-cadherin, occludin and claudin genes. For instance, Peinado et al. (supra (2004)) disclosed assaying Snail transcriptional activity using a reporter gene system in which the proximal promoter of the murine E-cadherin gene is operably fused to a luciferase cDNA. See also De Craene et al. (supra (2004), Barrallo-Gimeno et al., *Development* 132:3151-3161 (2005) and De Craen et al., *Cancer Res.* 65:6237-6244 (2005) for other genes repressed by Snail.

Snail activity may be measured by any assay intended for assessing binding. Such assays may be either direct or indirect measures of Snail activity, and may be done in vitro, in vivo or ex vivo. Exemplary assays include, but are not limited to: gel mobility shift assays, filter binding assays, transcriptional run-off assays, competitive binding assays, protein-protein binding assays, cellular response assays and reporter gene assays. In vivo assays may use cells that possess endogenous Snail activity or recombinant cells in which Snail activity is encoded and expressed by a heterologous nucleotide. Likewise, the Snail target molecule may be an endogenous nucleic acid or protein or encoded by a heterologous nucleotide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under-expressed or not expressed at all.

Prognostic Assays

As used herein, the terms "recurrence" and "relapse" refer to latent tumor cells that survive despite treatment, and reestablish malignant growth. Such latent tumor cells may be present at the original tumor site(s) or distant to it. The phrase "latent tumor cells" is used interchangeably herein with the phrase "dormant tumor cells."

As used herein, "metastasis" refers to the presence of actively growing tumor cells spread to sites distant from the primary tumor site.

The distinction between recurrence and metastasis is important because the mechanisms that allow latent tumor cells, either local or distant, to survive and ultimately reestablish malignant growth are likely to be distinct from those that permit actively growing tumor cells to invade and spread to distant sites. While metastasis is a sine qua non of distant spread, it is not required for local recurrence. Moreover, even in the case of distant recurrence, the mechanisms that permit metastatic cells to remain in a dormant state and then reemerge at a later time are not the same as those that permit distant spread.

In one embodiment of the invention, in order to determine the risk of breast cancer recurrence in a subject diagnosed with breast cancer, the expression of Snail is measured in a breast cancer tumor sample from the subject. In another embodiment, the likelihood of a recurrence-free survival in a subject with breast cancer is assessed, based on the expression of Snail is measured in a breast cancer tumor sample from the subject. Prognostic assays may be used for prognostic or predictive purposes to thereby prophylacticly treat an individual prior to the recurrence of breast cancer, or to help inform the health care provider with regard to decisions about how aggressively and with what therapeutics the breast cancer treatment should be for a subject. In one aspect, the breast cancer tumor sample is obtained from a subject whose breast cancer is locally advanced at the time of diagnosis. In another aspect, the breast cancer tumor sample is obtained from a subject who is lymph-node negative at the time of diagnosis of breast cancer. In yet another aspect, a second marker of breast cancer recurrence is also assessed, e.g., selected from the group consisting of tumor size, tumor grade, ER status and HER2 status.

Furthermore, using the prognostic methods described herein, the present invention provides methods for determining whether a subject may or should be administered with a specific agent (e.g., an antagonist, an agonist, peptidomimetic, protein, peptide, nucleic acid, small molecule, or other drug candidate) or class of agents (e.g., agents of a type that decrease Snail expression or Snail activity) to effectively treat or prevent breast cancer recurrence associated with high Snail expression or Snail activity. Specifically, a subject diagnosed with breast cancer at high risk of recurrence, according to the methods of the present invention, are thereby identified as candidates for treatment using a specific agent or class of agents that decrease Snail expression or Snail activity.

In another embodiment, the present methods determine if a specific agent or class of agents may or should be administered prophylacticly to prevent or delay recurrence of breast cancer in subjects at high risk of recurrence, as assessed by the methods herein. Specifically, a subject diagnosed with breast cancer at high risk of recurrence, according to the methods of the present invention, are thereby identified as a candidate for prophylactic treatment using a specific agent or class of agents that decrease Snail expression or Snail activity.

In another embodiment, the present methods assess the likely effectiveness of a treatment for reducing the risk of breast cancer recurrence in subjects at high risk of recurrence by measuring the expression of Snail before, during and after the treatment. Specifically, a treatment that results in the reduction of Snail expression or Snail activity is identified as likely to be effective.

For the purposes of the methods of the present invention, expression of Snail is divided into two categories: low expression and high expression. "High expression" or "high level of expression" or "overexpression" of Snail is indicative of an increased risk of breast cancer recurrence. "Low expression" or "low level of expression" of Snail is indicative of an increased likelihood of a recurrence-free survival. No recurrence was found in a subject in any analysis to be associated with a low level of expression of Snail. While high and low expression levels are specific for the particular platform or method used to determine expression levels (see, for instance, "Survival Analysis" in the materials and methods of the Examples), overall, within a group of patients having comparable disease characteristics, those patients whose tumors have higher levels of Snail expression have a worse prognosis or lower predicted levels of survival. The determination of whether the level of Snail expression is high or low, means as compared to a known or previously established standard level of Snail expression accepted in or acceptable to the art, or as compared to a previously recorded level of Snail expression for the subject being tested. Standards are established for this purpose, e.g., as set forth in van't Veer et al., supra (2002); Sorlie et al., supra (2003); Ma et al., supra (2004); and Wang et al., supra (2005)), (each is expressly incorporated by reference for this purpose) complete with hazard ratios and comparisons recognized by one of ordinary skill for purposes of determining the level of Snail expression in a sample as compared to normal levels for the general population or as compared with average levels for subjects diagnosed with breast cancer without an elevation of Snail. For example, in one embodiment, a Snail expression level of elevation >1.0 is significant, as shown in the cited references, as is an increase of more than 10%, 20%, 30%, 50%, or 100% over normal (meaning the standard). Conversely, subjects with tumors with lower levels of Snail expression have a better prognosis or better predicted levels of survival with respect to disease recurrence. A non-limiting example of a group of patients with comparable disease characteristics is a group of patients whose breast cancer is lymph-node negative. Another non-limiting example is a group of patients whose breast cancer is lymph-node negative and ER positive. Thus, an "increased risk" of breast cancer recurrence refers to a higher chance or probability of disease recurrence as compared to another patient having comparable disease characteristics. Similarly, an increased likelihood of recurrence-free survival refers to a lower chance or probability of disease recurrence as compared to another patient having comparable disease characteristics.

As used herein, a "breast cancer tumor sample" or "breast tissue sample" refers to a sample of breast tissue or fluid isolated from an individual diagnosed with breast cancer. Such samples are primary isolates (in contrast to cultured cells) and may be collected by any non-surgical means, including, but not limited to ductal lavage, fine needle aspiration, needle biopsy, the devices and methods described in U.S. Pat. No. 6,328,709, or any other suitable means recognized in the art. Alternatively, the "breast cancer tumor sample" may be collected by an invasive method, including, but not limited to, surgical biopsy.

As used herein, "measuring the expression of Snail" encompasses both direct and indirect measurements of Snail gene expression. Methods for direct measurement of Snail gene expression include, but are not limited to: reverse transcriptase PCR(RT-PCR) assays, quantitative RT-PCR (QRT-PCR) assays, and hybridization assays, including in situ hybridization, Northern hybridizations, microarrays and genome chips. Indirect measurements of Snail gene expression include assessing downstream effect of Snail gene expression, such as Snail protein levels and Snail activity. Methods for indirect measurement of Snail gene expression include, but are not limited to: transcription assays, radioimmunoassays, immunohistochemistry assays, competitive-binding assays, image-based methods (including used of labeled ligand, e.g., a Snail DNA binding site), Western Blot analyses, ELISA assays and proteomic approaches, two-dimensional gel electrophoresis (2D electrophoresis) and non-gel based approaches, such as mass spectrometry or protein interaction profiling.

Using all or a portion of a nucleic acid sequence of Snail as a hybridization probe, nucleic acid methods may be used to detect levels of Snail mRNA. Polymerase chain reaction (PCR) and other nucleic acid methods, such as ligase chain reaction (LCR) and nucleic acid sequence based amplification (NASBA), may also be used. For example, reverse-transcriptase PCR(RT-PCR) is a powerful technique, which may be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR may thus reveal by amplification the presence of a single species of mRNA. QRT-PCR allows quantification of starting amounts of RNA templates.

Hybridization to clones or oligonucleotides arrayed on a solid support (i.e., gridding) may be used to both detect the expression of and quantitate the level of expression of the Snail gene. In this approach, all or a portion of a cDNA encoding the Snail gene is fixed to a substrate. The substrate may be of any suitable type including, but not limited to, glass, nitrocellulose, nylon or plastic. At least a portion of the DNA encoding the Snail gene is attached to the substrate and then incubated with the analyte, which may be RNA or a complementary DNA (cDNA) copy of the RNA, isolated from the breast cancer tumor sample. Hybridization between the substrate-bound DNA and the analyte may be detected and quantitated by several means including, but not limited to, radioactive labeling or fluorescence labeling of the analyte or a secondary molecule designed to detect the hybrid. Quantitation of the level of gene expression may be done by comparison of the intensity of the signal from the analyte compared with that determined from known standards. The standards may be obtained by in vitro transcription of the target gene, quantitating the yield, and then using that material to generate a standard curve.

Because the invention relies upon the measurement of the expression of Snail, one embodiment of the invention involves determining expression by hybridization of mRNA, or an amplified or cloned version thereof, from a sample to a polynucleotide that is unique to a the Snail gene sequence. Preferred polynucleotides of this type contain a sequence that is, at least, about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. More preferred are polynucleotides that contain a sequence that is at least or about 50, at least or about 100, at least about or 150, at least or about 200, at least or about 250, at least or about 300, at least or about 350, or at least or about 400 basepairs of a gene sequence that is not found in other gene sequences. The term "about" as used in the preceding sentence refers to an increase or decrease of 10% from the stated numerical value. Such polynucleotides are also be referred to as polynucleotide probes that are capable of hybridizing to sequences of Snail, or unique portions thereof, described herein. Preferably, the sequences are those of mRNA encoded by Snail genes, the corresponding cDNA to such mRNAs, and/or amplified versions of such sequences. In certain embodiments of the invention, the polynucleotide probes are immobilized on an array, other devices, or in individual spots that localize the probes.

In another embodiment, Snail gene expression is determined by assessing the extent of Snail activity. Snail activity may be measured in any assay known to measure binding, including, but not limited to, gel mobility shift assays, competitive-binding assays and transcriptional assays. Transcription assays may use a gene regulated by Snail, or may use a promoter of such a gene operably fused to a reporter gene.

As used herein, the term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence. "In-frame fusion" refers to two or more coding sequences linked to each other such that each sequence is expressed and translated as a single polypeptide chain.

Alternatively, and in another embodiment of the invention, gene expression is determined by analysis of expressed Snail protein in a breast cancer tumor sample by use of one or more antibodies specific for one or more epitopes of Snail. Such antibodies are preferably labeled to permit their easy detection after binding to the gene product. The term "antibody," as used herein, refers to an immunoglobulin molecule which is able to specifically bind to a specific epitope on an antigen. Antibodies may be intact immunoglobulins derived from natural sources or from recombinant sources and may be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, intracellular antibodies ("intrabodies"), as well as single chain antibodies (scFv) and humanized antibodies (Harlow et al., *Using Antibodies: A Laboratory Manual*, Cold Spring Harbor Laboratory Press, Cold Spring Harbor, N.Y. (1999); Harlow et al., *Antibodies: A Laboratory Manual*, Cold Spring Harbor Laboratory Press, Cold Spring Harbor, N.Y. (1988); Houston et al., *Proc. Natl. Acad. Sci. USA* 85:5879-5883 (1988); Bird et al., *Science* 242:423-426 (1988)). As used herein, a "neutralizing antibody" is an immunoglobulin molecule that binds to and blocks the biological activity of the antigen.

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The generation of polyclonal antibodies is accomplished by inoculating the desired animal with the antigen and isolating antibodies which specifically bind the antigen.

Monoclonal antibodies directed against full length or peptide fragments of a protein or peptide may be prepared using any well-known monoclonal antibody preparation procedures, such as those described, for example, in Harlow et al. (supra (1988)), Tuszynski et al. (*Blood,* 72:109-115 (1988)) and U.S. Patent Publication No. 20030224490 for generation of human monoclonal antibodies. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (*Critical Rev. Immunol.* 12(3,4): 125-168 (1992)) and the references cited therein. Further, the antibody of the invention may be "humanized" using the technology described in Wright et al., (supra (1992)) and in the references cited therein, and in Gu et al. (*Thrombosis and Hematocyst* 77(4):755-759 (1997)).

Phage antibody library technology may also be used. The procedures for making a bacteriophage library comprising heterologous DNA are well known in the art and are described, for example, in Sambrook et al. (*Molecular Cloning: A Laboratory Manual*, Cold Spring Harbor Laboratory Press, Cold Spring Harbor, N.Y. (1989)). Processes, such as those described above, have also been developed for the production of human antibodies using M13 bacteriophage display (Burton et al., *Adv. Immunol.* 57:191-280 (1994)). This procedure immortalizes DNA encoding human immunoglobulin, rather than cells which express human immunoglobulin.

The procedures just presented describe the generation of phage which encode the Fab portion of an antibody molecule. However, the methods of the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., (*J. Mol. Biol.* 222:581-597 (1991)). Panning of phage so generated for the isolation of a desired antibody is conducted in a manner similar to that described for phage libraries comprising Fab DNA.

The invention is also construed to include synthetic phage display libraries in which the heavy and light chain variable regions may be synthesized, such that they include nearly all possible specificities (Barbas, *Nat. Med.* 1:837-839 (1995); de Kruif et al., *J. Mol. Biol.* 248:97-105 (1995)).

Assays of the present invention include various immunoassays, for example, immunohistochemistry assays, immunocytochemistry assays, ELISA, capture ELISA, sandwich assays, enzyme immunoassay, radioimmunoassay, fluorescent immunoassay, and the like, all of which are known to those of skill in the art. See e.g., Harlow et al., supra (1988); Harlow et al., supra (1999).

Enzyme-linked immunoadsorbent assays (ELISA) may be used in the methods, assays and kits of the present invention. In an ELISA assay, proteins or peptides are immobilized onto a selected surface, preferably a surface exhibiting a protein affinity, such as the wells of a polystyrene microtiter plate. After washing to remove incompletely adsorbed material, it is desirable to bind or coat the assay plate wells with a nonspecific protein that is known to be antigenically neutral with regard to the test antisera, such as bovine serum albumin (BSA), casein or solutions of milk powder. This allows for blocking of nonspecific adsorption sites on the immobilizing surface, and thus, reduces the background caused by nonspecific binding of antisera onto the surface.

After binding of antigenic material to the well, coating with a non-reactive material to reduce background, and washing to remove unbound material, the immobilizing surface is contacted with the antisera (or clinical or biological sample to be tested) in a manner conducive to immune complex (antigen/antibody) formation. Such conditions preferably include diluting the antisera with diluents, such as BSA, bovine gamma globulin (BGG), phosphate buffered saline (PBS)/Tween, and the like. These added agents also tend to assist in the reduction of nonspecific background. The layered antisera is then allowed to incubate for about greater than one hour, at temperatures preferably on the order of about 25° to 27° C. Following incubation, the antisera-contacted surface is washed so as to remove non-immunocomplexed material. A preferred washing procedure includes washing with a solution, such as PBS/Tween, or borate buffer.

Following formation of specific immunocomplexes between the test sample and the bound antigen, and subsequent washing, the occurrence and amount of immunocomplex formation may be determined by subjecting the immunocomplexes to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a biotin or peroxidase-conjugated anti-appropriate-animal IgG for a period of time and under conditions which favor the development of immunocomplex formation (e.g., incubation for about 2 hours at room temperature in a PBS-containing solution, such as PBS-Tween).

After incubation with the second tagged antibody, and subsequent to washing to remove unbound material, the amount of label is quantified by incubation with a chromogenic substrate, such as urea and bromocresol purple, or 2,2'-azino-di-(3-ethyl-benzthiazoline-6-sulfonic acid) [ABTS] and hydrogen peroxide ($H_2O_2$), in the case of peroxidase as the enzyme label. Quantification is then achieved by measuring the degree of color generation, e.g., using a visible spectra spectrophotometer.

Kits

In another embodiment of the invention, kits for measuring the expression level of Snail in a breast cancer tumor sample are provided. For example, one kit comprises a labeled compound or agent capable of detecting Snail mRNA in a breast cancer tumor sample, means for determining the amount of mRNA in the sample, and instructional material. The labeled compound or agent is typically an oligonucleotide that hybridizes to a Snail nucleic acid molecule or a pair of primers useful for amplifying a Snail nucleic acid molecule.

In yet another embodiment, a kit for measuring the expression level of Snail by detecting the amount of Snail in a breast cancer tumor sample is provided. Preferably, detection of the level of Snail protein is by means of an antibody against Snail. In this embodiment, the kit includes a negative control solution of Snail protein at a concentration of about the concentration of Snail protein in a breast cancer tumor sample of a mammal at low risk of breast cancer recurrence, a positive control solution of Snail protein at a concentration of about the concentration of Snail protein present in a breast cancer tumor sample of a mammal at high risk of breast cancer recurrence, an antibody directed against the Snail protein and instructional material. Optionally, the kit further includes a sample container for carrying a breast cancer tumor sample from a mammal. In another embodiment, this kit further comprises a second antibody that binds to the first antibody and is conjugated to a detectable agent.

As used herein, "instructional material" includes a publication, a recording, a diagram, or any other medium of expression which may be used to communicate the usefulness of assessing Snail expression for prognostic purposes for subjects with breast cancer. The instructional material of the kit of the invention may, for example, be affixed to one of the containers which contain control solutions of Snail protein or an antibody against Snail protein or be shipped together with the containers which contain Snail protein control solutions. Alternatively, the instructional material may be shipped separately from the containers, with the intention that the instructional material and the control solutions and antibody be used cooperatively by the recipient.

Additional Methods

The methods of the invention may in other embodiments also be used to detect genetic lesions or mutations in a Snail gene, thereby determining if a subject with the subject gene is at risk for a breast cancer recurrence. Such methods include detecting in a sample of cells from the subject, the presence or absence of a genetic-based lesion or mutation, which is characterized by overexpression of the Snail gene. For example, such genetic lesions or mutations are detected by ascertaining the existence of at least one of: (1) a deletion of one or more nucleotides from a Snail gene; (2) an addition of one or more nucleotides to a Snail gene; (3) a substitution of one or more nucleotides of a Snail gene; (4) a chromosomal rearrangement of a Snail gene; (5) an increase in the level of a messenger RNA transcript of a Snail gene; (6) an aberrant modification of a Snail gene, such as of the methylation pattern of the genomic DNA; (7) the presence of a non-wild-type splicing pattern of a messenger RNA transcript of a Snail gene; (8) a non-wild-type level of a Snail protein; and (9) an inappropriate post-translational modification of a Snail protein. As described herein, there are many assay techniques known in the art that may be used for detecting lesions in a Snail gene. Any cell type or tissue in which Snail proteins are expressed may be utilized in the prognostic assays described herein. Preferably, the cell or tissue is a breast tissue sample, more preferably, a breast cancer tumor sample, and more preferably a human breast cancer tumor sample.

Exemplary methods for detecting lesions include, but are not limited to: the use of a probe/primer in a polymerase chain reaction (PCR); alterations in restriction enzyme cleavage patterns of DNA compared to wild-type Snail DNA; the use of sequence specific ribozymes; hybridization methods; sequencing; protection from cleavage agents to detect mismatched bases; alterations in electrophoretic mobility (e.g., single-strand conformation polymorphism); denaturing gradient gel electrophoresis (DGGE); selective amplification; and selective primer extension.

Alternative amplification methods include self-sustained sequence replication (Guatelli et al., *Proc. Natl. Acad. Sci. USA* 87:1874-1878 (1990)), transcriptional amplification system (Kwoh et al., *Proc. Natl. Acad. Sci. USA* 86:1173-

1177 (1989)), Q-Beta Replicase (Lizardi et al., *Bio/Technology* 6:1197 (1988)), or any other nucleic acid amplification method. This is followed by the detection of the amplified molecules using techniques well known to those of skill in the art. Selected detection schemes are especially useful for the detection of nucleic acid molecules, if such molecules are present in very low numbers.

Modulators of Snail Expression and Snail Protein

In another embodiment, the invention provides methods to identify modulators of Snail expression or Snail activity. Modulators which reduce either Snail expression or Snail activity are potential therapeutic compounds for use in the treatment of recurrent breast cancer or prophylactic treatment of breast cancer in subjects at high risk of recurrence, preferably where the breast cancer is characterized by high Snail expression. The modulators are also extremely useful as research tools in further studying the role of Snail expression and Snail activity in development or in other disorders or diseases, for instance, those which are characterized by EMT. Therefore, methods of identifying such modulators are useful.

The terms "modulating expression" "inhibiting expression" and "activating expression" of a gene refer to the ability of a molecule to activate or inhibit transcription of a gene. Activation includes prevention of transcriptional inhibition (i.e., prevention of repression of gene expression) and inhibition includes prevention of transcriptional activation (i.e., prevention of gene activation). The term "modulating Snail activity" refers to the ability of a molecule to increase or reduce Snail activity, as defined elsewhere herein. Such a molecule may increase or reduce Snail activity directly or indirectly. For instance, a molecule may modify an effector upstream of Snail in the relevant signaling pathway, such that Snail activity is reduced or increased. For example, GSK-3β inhibits Snail transcription and also promotes its nuclear export and proteasome-dependent degradation by a phosphorylation-dependent mechanism (Zhou et al., *Nature Cell Biol.* 6: 931-940 (2004); Bachelder et al., *J. Cell Biol.* 168: 29-33 (2005)). Accordingly, inhibition of GSK-3β activity by the PI3K/AKT, MAPK and Wnt signaling pathways promotes Snail stabilization and activation. In addition, phosphorylation of Snail by Pak1—which is activated by PI3K via AKT and the small GTPase, Rac (Tang et al., *J. Biol. Chem.* 275: 9106-9109 (2000))—enhances Snail's repressor activity by promoting its nuclear accumulation (Yang et al., *Can. Res.* 65: 3179-3184 (2005)). As such, the development of molecules that target these upstream pathways may provide a dual mechanism for the inhibition of Snail activity both by activating GSK-3β and inhibiting Pak1. Similarly, a molecule may modify an effector downstream of Snail such that Snail activity is reduced or increased.

Modulation may be assayed by determining any parameter that is indirectly or directly affected by the expression of the Snail gene. Such parameters include, e.g., changes in RNA or protein levels, changes in protein activity, changes in downstream, Snail-regulated gene expression (such as down-regulation of E-cadherin or occludin expression), changes in reporter gene transcription (luciferase, CAT, β-galactosidase, β-glucuronidase, GFP (see, e.g., Mistili et al., *Nature Biotechnology* 15:961-964 (1997)); cell growth, and cell morphology including transitions, such as epithelial-to-mesenchymal, and expression of biomarker associated with EMT, including those set forth in the examples below. These assays include in vitro, in vivo, and ex vivo methods. Such functional effects may be measured by any means known to those skilled in the art, e.g., measurement of RNA or protein levels, measurement of RNA or protein stability, identification of downstream or reporter gene expression, e.g., via chemiluminescence, fluorescence, phosphorescence, colorimetric reactions, antibody binding, inducible markers, ligand binding assays; and the like.

The assay for Snail nucleic acid expression may also involve direct assay of nucleic acid levels, such as mRNA levels, or expression of genes that are up- or down-regulated in response to Snail may also be assayed. In this embodiment, the regulatory regions (i.e., promoters) of these genes may be operably linked to a reporter gene, such as luciferase.

Thus, modulators of Snail gene expression may be identified in a method wherein a host cell is contacted with a candidate compound (e.g., peptides, peptidomimetics, nucleic acids, small molecules, or other drugs) and the expression of mRNA determined. The level of expression of Snail mRNA in the presence of the candidate compound is compared to the level of expression of Snail mRNA in the absence of the candidate compound. The candidate compound may then be identified as a modulator of nucleic acid expression based on this comparison and be used, for example, to treat breast cancer in patient at high risk of recurrence. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression. Potential therapeutics for treating breast cancer recurrence or breast cancer likely to recur are expected to be inhibitors of Snail gene expression. In some aspects, the test compound is a nucleic acid, such as an antisense molecule directed against Snail, or an siRNA molecule directed against mRNA encoding Snail.

By "host cell" is meant a cell that contains Snail, or an expression vector or nucleic acid encoding Snail. The host cell typically supports the replication or expression of the expression vector. Host cells may be prokaryotic cells, such as *E. coli*, or eukaryotic cells, such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

An "expression vector" is a nucleic acid construct, generated recombinantly or synthetically, with a series of specified nucleic acid elements that permit transcription of a particular nucleic acid in a host cell, and optionally, integration or replication of the expression vector in a host cell. The expression vector may be part of a plasmid, virus, or nucleic acid fragment, of viral or non-viral origin. Typically, the expression vector includes an "expression cassette," which comprises a nucleic acid to be transcribed operably linked to a promoter. The term expression vector also encompasses naked DNA operably linked to a promoter.

A "promoter" is defined as an array of nucleic acid control sequences that direct transcription. As used herein, a promoter typically includes necessary nucleic acid sequences near the start site of transcription, such as, in the case of certain RNA-polymerase-II-type promoters, a TATA element, enhancer, CCAAT box, SP-1 site, etc. As used herein, a promoter also optionally includes distal enhancer or repressor elements, which may be located as much as several thousand base pairs from the start site of transcription. Promoters often have an element that is responsive to transactivation by a DNA-binding moiety such as a polypeptide, e.g., a nuclear receptor, Gal4, the lac repressor and the like.

A "constitutive" promoter is a promoter that is active under most environmental and developmental conditions. An "inducible" promoter is a promoter that is active under certain environmental or developmental conditions.

The invention provides, in yet another embodiment, a method for identifying modulators, i.e., candidate or test compounds or agents (e.g., peptides, peptidomimetics, nucleic acids, small molecules, or other drugs), that directly or indirectly have a stimulatory or inhibitory effect on Snail activity. A direct modulator may bind to Snail protein and thereby modulate its activity. An indirect modulator may affect Snail activity by altering upstream effectors, such as post-translational modification effectors, or downstream effectors, for instance, factors to which Snail binds and/or factors involved in Snail-specific transcriptional repression, thereby modulating Snail activity. The methods of the invention are not limited by the type of test compound used in the assay. The test compound may thus be a synthetic or naturally-occurring molecule, which may comprise a peptide or peptide-like molecule, or it may be any other molecule, either small or large, which is suitable for testing in the assay.

The test compounds of the present invention may be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, *Anticancer Drug Des.* 12:145 (1997)). Examples of methods for the synthesis of molecular libraries may be found in the art, for example, in: DeWitt et al., *Proc. Natl. Acad. Sci. USA* 90:6909-6913 (1993); Erb et al., *Proc. Natl. Acad. Sci. USA* 91:11422-11426 (1994); Zuckermann et al., *J. Med. Chem.* 37:2678-2685 (1994); Cho et al., *Science* 261:1303-1305 (1993); Carell et al., *Angew. Chem. Int. Ed. Engl.* 33:2059-2061 (1994); Carell et al., *Angew. Chem. Int. Ed. Engl.* 33:2061-2064 (1994); and Gallop et al., *J. Med. Chem.* 37:1233-1251 (1994). Libraries of compounds may be presented in solution (e.g., Houghten, *Bio/Techniques* 13:412-421 (1992)), or on beads (Lam, *Nature* 354:82-84 (1991)), chips (Fodor (1993) *Nature* 364: 555-556), bacteria (U.S. Pat. No. 5,223,409), spores (U.S. Pat. Nos. 5,571,698; 5,403,484; and 5,223,409), plasmids (Cull et al., *Proc. Natl. Acad. Sci. USA* 89:1865-1869 (1992)), or phage (Scott and Smith, *Science* 249:386-390 (1990); Devlin, *Science* 249:404-406 (1990); Cwirla et al., *Proc. Natl. Acad. Sci. USA* 87:6378-6382 (1990); and Felici, *J Mol. Biol.* 222:301-310 (1991)).

Methods for measuring the expression of Snail, directly or indirectly, are discussed above. Determining the ability of the test compound to bind to the Snail protein may be accomplished, for example, by coupling the test compound with a radioisotope or enzymatic label, such that binding of the test compound to the Snail protein, or biologically active portion thereof, may be determined by detecting the labeled compound in a complex. For example, test compounds may be labeled with $^{125}I$, $^{35}S$, $^{14}C$, or $^{3}H$, either directly or indirectly, and the radioisotope detected by direct counting of radioemission or by scintillation counting. Alternatively, test compounds may be enzymatically labeled with, for example, horseradish peroxidase, alkaline phosphatase, or luciferase, and the enzymatic label detected by determination of conversion of an appropriate substrate to product.

In a similar manner, one may determine the ability of the Snail protein to bind to or interact with a Snail target molecule as disclosed herein. In a preferred embodiment, the ability of the Snail protein to bind to or interact with a cognate DNA binding site may be determined by monitoring the expression of a reporter gene operably linked to a Snail cognate binding site. Alternatively, binding is monitored by detecting a Snail-modulated cellular response, for example, EMT.

In yet another embodiment, an assay of the present invention is a cell-free assay including contacting a Snail protein, or biologically active portion thereof, with a test compound and determining the ability of the test compound to bind to the Snail protein, or biologically active portion thereof. Binding of the test compound to the Snail protein may be determined either directly or indirectly as described herein. In one embodiment, the assay includes contacting the Snail protein, or biologically active portion thereof, with a known compound that binds with it to form an assay mixture, contacting the assay mixture with a test compound, and determining the ability of the test compound to preferentially bind to Snail protein, or biologically active portion thereof, as compared to the known compound.

In the above-mentioned assays, it may be desirable to immobilize either a Snail protein or its target molecule to facilitate separation of complexed from uncomplexed forms of one or both of the molecules, as well as to accommodate automation of the assay. In one embodiment, a fusion protein may be provided that adds a domain to Snail or to a protein target molecule that allows one or both of the proteins to be bound to a matrix. For example, glutathione-S-transferase/kinase fusion proteins or glutathione-S-transferase/target fusion proteins may be adsorbed onto glutathione Sepharose beads (Sigma-Aldrich Co., St. Louis, Mo.) or glutathione-derivatized microtiter plates. The test compound, or the test compound and either the nonadsorbed target protein or Snail protein, is added, and the mixture incubated under conditions conducive to complex formation (e.g., at physiological conditions for salt and pH). Following incubation, the beads or microtiter plate wells are washed to remove any unbound components, and complex formation is measured either directly or indirectly, for example, as described above. Alternatively, the complexes may be dissociated from the matrix, and the level of Snail binding or activity determined using standard techniques.

Other techniques for immobilizing proteins on matrices are also suitable for screening assays of the invention. For example, either Snail protein or its target molecule may be immobilized utilizing conjugation of biotin and streptavidin. Alternatively, antibodies reactive with a Snail protein or target molecules, but which do not interfere with binding of the Snail protein to its target molecule, may be derivatized to the wells of the plate, and unbound target or Snail protein trapped in the wells by antibody conjugation. Methods for detecting such complexes, in addition to those described above for the GST-immobilized complexes, include immunodetection of complexes using antibodies reactive with the Snail protein or target molecule.

Compounds which are identified using the methods of the invention are candidate therapeutic compounds for treatment of a subject diagnosed with breast cancer, and particularly, those breast cancers expressing Snail at high levels, and thus, as the data herein demonstrates, at high risk for recurrence. Additionally, the compounds identified by the methods of the invention are useful in further studying the Snail transcriptional repression pathway in development, in breast cancer and in other disorders or diseases affected by Snail, for instance, those characterized by EMT. Compounds identified in vitro are then tested for activity against Snail expression or Snail activity in vivo in animals. In one aspect, compounds are tested in non-human animals, preferably non-human mammals. In another aspect, compounds are tested in humans. Essentially, the compound is administered to the non-human animal or human by any of the routes described herein, and the effect of the compound is assessed by clinical and symptomatic evaluation. Such assessment is well known to the practitioner in the field of developmental biology or those studying the effect of cancer drugs.

A compound may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient. The pharmaceutically acceptable carrier is selected on the basis of the selected route of administration and standard pharmaceutical practice. The compound may be formulated into dosage forms according to standard practices in the field of pharmaceutical preparations. See, for instance, Gennaro, ed., *Remington's Pharmaceutical Sciences,* 18th Ed., (1990) Mack Publishing Co., Easton, Pa. Suitable dosage forms comprise, for example, tablets, capsules, solutions, parenteral solutions, troches, suppositories, or suspensions.

Routes of administration for a compound or pharmaceutical composition comprising a compound include all conventional routes known in the art. Such routes include but are not limited to: aerosol, oral, nasal, subcutaneous, transdermal, intramuscular, intravenous, intraperitoneal, intrapulmonary, intratumoral, intratracheal, directly to a localized region surrounding a target site, directly to a tumor bed, or a combination of routes. The administration may take place in a single dose or in a dose repeated one or more times after a certain time interval. Precise formulations and dosages will depend on the nature of the compound and may be determined using standard techniques, by a pharmacologist of ordinary skill in the art.

Reducing Snail Expression

In yet another embodiment, the invention provide methods of reducing the expression of Snail in a cell. The cell may be from a cell line, a cell removed from an animal, or a cell within an animal. Preferably, the cell is a breast cancer cell. More preferably, the cell is a breast cancer tumor cell, for instance, from a breast cancer tumor cell line. More preferably still, the cell is a primary breast cancer tumor cell. Preferably, the cell is human. As used herein, "reduce" means a lessening or reduction or prophylactic decrease in a function, such as the expression of Snail in a cell or activity of the Snail protein, or the prevention of the detrimental effect of the disorder in the patient receiving the therapy, thereby resulting in "protecting" the patient. A "sufficient amount" or "effective amount" or "therapeutically effective amount" of an administered composition is that volume or concentration which causes or produces a measurable change from the pre-administration state in the cell or patient. "Inhibition" or "blocking" refer to a statistically significant reduction in expression of Snail in a cell or activity of the Snail protein, as compared with a selected standard of activity or for cells or tissues without the addition of the selected compound (including a peptide, or an active fragment thereof) that effects the reduction. "Preventing" refers to effectively 100% levels of prophylactic inhibition. Preferably, the reduced levels (meaning a lower concentration of, e.g., Snail, than was present before modulation resulting from methods disclosed herein or before its expression was down-regulated in the patient) refers to a lowered amount or decreased activity by at least 5%, or by at least 10%, or by at least 20%, or by at least 50%, or even by 80% or greater, including in a dose-dependent manner.

Methods of reducing the expression of Snail in a cell have numerous uses. They are useful for therapeutic applications, for instance, for subjects diagnosed with breast cancer at high risk of recurrence. As used herein, "therapeutic" is defined as alleviating one or more symptoms of a disease. As demonstrated by the data herein, one of the symptoms of breast cancer at high risk of recurrence is overexpression of Snail. The methods of reducing expression of Snail in a cell are also useful as research tools in studying the role of Snail expression and Snail activity in other disorders and diseases, for instance those characterized by EMT, as well as in developmental biology. In this embodiment, the cell is preferably a non-human animal cell, more preferably, a non-human mammal cell.

Generally, reducing expression of Snail encompasses reducing or eliminating transcription of Snail, reducing or eliminating translation of Snail mRNA, and reducing or eliminating Snail activity by administration of an inhibitor. Reducing transcription of Snail may be achieved, for instance, by knocking out the Snail gene or its nucleic acid transcriptional elements or by inhibiting transcription of the Snail gene. Inhibition of Snail gene expression may be direct or indirect, for instance, by modifying the activity of a Snail-gene-specific transcriptional factor, or modifying an upstream or downstream effector necessary for Snail activity. Reducing translation of Snail mRNA includes, for instance, reducing the stability or half-life of Snail mRNA or specifically inhibiting translation of Snail mRNA. Reducing Snail activity includes, for instance, inhibiting binding to a target molecule (its cognate DNA binding site and/or other transcriptional repression complex proteins), reducing the half-life of Snail protein (i.e., increasing degradation) or modifying effectors downstream of Snail such that Snail activity is reduced or precluded.

Reducing expression may be achieved by administering an effective amount of an inhibitor of Snail expression. As used herein, an "effective amount" of an inhibitor is that amount of the inhibitor that is sufficient to reduce or eliminate Snail expression, thereby preventing or delaying the recurrence of breast cancer, or preventing, reducing or delaying EMT.

In one embodiment, the inhibitor is selected from the group consisting of a small interfering RNA (siRNA), a microRNA, an antisense nucleic acid, a ribozyme, an expression vector encoding a transdominant negative mutant, an intracellular antibody, a peptide and a small molecule. Preferably, the inhibitor is an siRNA. In certain embodiments, the inhibitor of Snail expression is encoded by an isolated polynucleotide cloned into an expression vector. The expression vector is selected from the group consisting of a plasmid DNA, a viral vector, a bacterial vector and a mammalian vector. Adenoviral vectors are particularly effective means for introducing genes into cells or tissues in vivo because of their high level of expression and efficient transformation of cells both in vitro and in vivo. In another aspect, the expression vector further comprises an integration signal sequence which facilitates integration of the isolated polynucleotide into the genome of a host cell.

Methods of inhibiting transcription of a gene are well known to one of skill in the art. For instance, knock-out vectors may be used to inhibit Snail expression. A "knock-out" vector of the invention comprises at least two sequences homologous to two portions of the nucleic acid which is to be deleted. The two sequences are homologous with sequences that flank the gene; that is, one sequence is homologous with a region at or near the 5' portion of the coding sequence of the nucleic acid encoding normal Snail and the other sequence is further downstream from the first. One skilled in the art would appreciate, based upon the disclosure provided herein, that the present invention is not limited to any specific flanking nucleic acid sequences. In the alternative, the targeting vector may comprise two sequences which remove some or all of, for example, normal Snail (i.e., a "knock-out" vector) or from a mammalian genome. A crucial feature of the targeting vector is that it comprise sufficient portions of two sequences located towards opposite, i.e., 5' and 3', ends, of the normal Snail open reading frame (ORF) to allow deletion/insertion by homologous recombination to occur such that all or a portion of the nucleic acid encoding normal Snail is deleted from a location on a mammalian chromosome.

The design of transgenes and knock-out targeting vectors is well-known in the art and is described in standard treatises by, e.g., Sambrook et al. (supra (1989)), Ausubel et al. (supra (1997)), and the like. The upstream and downstream portions flanking or within the Snail coding region to be used in the targeting vector may be easily selected based upon known methods and following the teachings disclosed herein. Armed with these sequences, one of ordinary skill in the art would be able to construct the transgenes and knock-out vectors useful in the methods of the invention.

Methods of reducing translation of mRNA are well known to one of skill in the art. Such methods include antisense methods, ribozymes or interfering RNA methods. Antisense nucleic acid molecules are DNA or RNA molecules that are complementary to some portion of an mRNA molecule. When present in a cell, antisense nucleic acids hybridize to an existing mRNA molecule and inhibit translation into a gene product. Inhibiting the expression of a gene using an antisense nucleic acid molecule is well known in the art (Marcus-Sekura, *Anal. Biochem.* 172:289 (1988)), as are methods to express an antisense nucleic acid molecule in a cell (U.S. Pat. No. 5,190,931).

The invention further encompasses inhibiting the expression of Snail using a ribozyme. Using ribozymes for inhibiting gene expression is well known to those of ordinary skill in the art (Cech et al., *J. Biol. Chem.* 267:17479-17482 (1992); Hampel et al., *Biochemistry* 28:4929-4933 (1989); U.S. Pat. No. 5,168,053). Ribozymes are catalytic RNA molecules with the ability to cleave other single-stranded RNA molecules. Ribozymes are known to be sequence specific, and can, therefore, be modified to recognize a specific nucleotide sequence (Cech, *J. Amer. Med. Assn.* 260:3030-3034 (1988)), allowing the selective cleavage of specific mRNA molecules.

In the alternative, RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved, and this sequence-specific degradation of mRNA results in gene silencing. See, for example, U.S. Pat. No. 6,506,559; Fire et al., *Nature* 391(19):306-311 (1998); Timmons et al., *Nature* 395:854 (1998); Montgomery et al., *TIG* 14(7):255-258 (1998); Engelke, D. R., Ed., *RNA Interference (RNAi) Nuts & Bolts of RNAi Technology*, DNA Press, Eagleville, Pa. (2003); and Hannon, G. J., Ed., *RNAi A Guide to Gene Silencing*, Cold Spring Harbor Laboratory Press, Cold Spring Harbor, N.Y. (2003). Soutschek et al. (*Nature* 432:173-178 (2004)) describe a chemical modification to siRNAs that aids in intravenous systemic delivery in mammals. Therefore, the present invention also includes methods of silencing a gene encoding Snail by using RNAi technology. Given the nucleotide sequence of Snail, one of ordinary skill in the art may also synthesize an antisense polynucleotide, ribozyme or siRNA without undue experimentation, provided with the disclosure and references incorporated herein.

Methods of reducing Snail activity are well known to one of ordinary skill in the art. Such methods include administering inhibitors that bind Snail and inhibit binding to its cognate DNA binding site or to another protein in a transcriptional repression complex. Inhibitors of Snail activity may directly or indirectly reduce or preclude Snail activity, preferably Snail's transcriptional repression activity. Inhibitors may, for instance, act on molecules downstream of Snail in the relevant signaling pathway, thereby indirectly reducing Snail activity. Inhibitors of Snail activity may be identified by the methods of the present invention described herein. Preferably, the molecule inhibits binding of Snail to its cognate DNA binding site.

In one embodiment, an neutralizing antibody may be administered such that it blocks Snail protein binding to a target molecule and/or Snail transcriptional repression in a mammal. Moreover, the invention encompasses administering a neutralizing antibody that specifically binds with Snail, or a nucleic acid encoding the antibody, wherein the antibody further comprises an intracellular retention sequence such that the antibody binds with Snail and prevents its transcriptional repression of genes, including, but not limited to, E-cadherin. Such antibodies, frequently referred to as "intrabodies", are well known in the art and are described in, for example, Marasco et al. (U.S. Pat. No. 6,004,490) and Beerli et al. (*Breast Cancer Res. Treat.* 38:11-17 (1996)). Thus, the invention encompasses methods comprising inhibiting Snail activity where Snail is overexpressed in a mammal.

The present invention is further described in the following examples. These examples are provided for purposes of illustration only, and are not intended to be limiting unless otherwise specified. The various scenarios are relevant for many practical situations, and are intended to be merely exemplary to those skilled in the art. These examples are not to be construed as limiting the scope of the appended claims. Thus, the invention should in no way be construed as being limited to the following examples, but rather, should be construed to encompass any and all variations which become evident in light of the teaching provided herein.

EXAMPLES

The materials and methods used in the examples are now described.

Animals and Tissues: MMTV-rtTA/TetO-NeuNT mice were engineered as previously described by Gunther et al., supra (2002); Moody et al., supra (2002)). Transgenic mice were housed under barrier conditions with a 12 hour light/dark cycle and access to food and water ad libitum. Induced animals were administered 2 milligram/milliliter (mg/ml) doxycycline (Sigma-Aldrich Co., St. Louis, Mo.) in their drinking water, which was replaced weekly. Animals were inspected for tumors weekly, and existing tumors were measured weekly. At the indicated times of sacrifice, animals were killed by $CO_2$ asphyxiation, and tissues were either snap frozen on dry ice for protein or RNA analysis, fixed in 4% paraformaldehyde for morphological and immunohistochemical analysis, or frozen in Optimal Cutting Temperature (OCT) compound for immunofluorescent analysis.

Histology: Mammary tumors were fixed overnight in 4% paraformaldehyde and were subsequently transferred to 70% ethanol (ETOH). For histological analysis, fixed tumors were then blocked in paraffin, sectioned, and stained with hematoxylin and eosin.

Immunohistochemistry: Tumor tissue was harvested from sacrificed or biopsied mice and fixed overnight in 4% paraformaldehyde, transferred to 70% ETOH, and embedded in paraffin. Five micrometer (μm) sections on ProbeOn® Plus (Fisher Scientific Instruments, Hampton, N.H.) slides were dewaxed in xylene, then sequentially rehydrated in 100%, 95%, and 70% ETOH, followed by phosphate buffered saline (PBS). Sections were pretreated in 2N HCl for 20 min at RT, washed twice in 0.1 M Borate buffer pH 8.5, and rinsed in PBS. Bromodeoxyuridine (BrdU) immunohistochemistry was performed using the Vectastain® Elite ABC Kit (Vector Laboratories, Burlingame, Calif.), rat anti-BrdU IgG (Vector Laboratories, Burlingame, Calif.), and a secondary biotinylated rabbit anti-rat IgG antibody, according to manufacturer's instructions. Sections were counterstained for 10 min in 0.5% (w/v) methyl green in 1.0 M NaOAc, pH 4.0.

For Neu/ErbB2 and CK8 IHC, paraffin-embedded tumors were sectioned at 5 μm and antigen retrieval was accomplished by microwaving in citrate buffer. Anti-ErbB2 and anti-CK8 antibodies (Cardiff) were detected using the Vectastain® Elite ABC Kit. Images were captured using a Kontronic camera model 8102 on an Olympus BH2 microscope (Olympus America, Melville, N.Y.), digitized using Photoshop® 6.0 (Adobe Systems Inc, San Jose, Calif.) with the Kontron ProgRes "plug-in" module, color enhanced and balanced for contrast.

Indirect Immunofluorescence: Tumor tissue was harvested, embedded in OCT compound and frozen. 8 μm tissue sections or cell lines were fixed in 4% paraformaldehyde for 10 minutes, washed in PBS, and permeabilized with 0.5% Triton-X-100 in PBS for 20 minutes. Cells were blocked in 3% BSA in PBS for one hour at room temperature and subsequently incubated overnight at 4° C. with primary antibody diluted in blocking buffer. Slides were washed 5× for 5 minutes in PBS, incubated with goat anti-rabbit, goat anti-mouse or goat anti-rat secondary antibodies (Invitrogen Molecular Probes, Carlsbad, Calif.) for one hour at room temperature, and washed again 5× in PBS. Slides were also counterstained for 10 minutes with 500 microgram/milliliter (μg/ml) Hoescht dye (Sigma-Aldrich Co., St. Louis, Mo.) dissolved in PBS. All microscopy was visualized on a Leitz DMRXE microscope (Leica, Wetzlar, Germany) and images were taken using the Spot RT™ Color Camera (Diagnostic Instruments, Sterling Heights, Mich.) with the Spot Advanced imaging program (Diagnostic Instruments, Sterling Heights, Mich.). The following primary antibodies were used as indicated 1:50 rat anti-Cytokeratin-8 (TROMA-1, Developmental Studies Hybridoma Bank, University of Iowa, Iowa City, Iowa), 1:100 rat anti-E-cadherin (clone ECCD2, 13-1900, Zymed Laboratories, Invitrogen, Carlsbad, Calif.), 1:100 rabbit anti-S100A4 (A 5114, DakoCytomation, Copenhagen, Denmark), 1:100 mouse anti-Fibronectin (610077, BD Transduction Laboratories™, BD Biosciences, San Jose, Calif.).

Northern Analysis: Snap-frozen tissue was homogenized in guanidine thiocyanate supplemented with 7 microliter/milliliter (μl/ml) 2-mercaptoethanol, and RNA was isolated by centrifugation through cesium chloride as previously described (Rajan et al., *PNAS, USA.* 93:13078-13083 (1996)). Total RNA (3 μg per blot) was separated on a 1% LE agarose gel, and passively transferred to GeneScreen (PerkinElmer NEN, Boston, Mass.). Northern hybridization was performed per manufacturer's instructions using PerfectHyb™ Plus Hybridization Buffer (Sigma-Aldrich Co., St. Louis, Mo.) and a $^{32}$P-labeled cDNA probe spanning the 3' end of the neu coding sequence and the 5' end of the IRES, or with cDNA probes spanning 300-600 bp fragments of the coding sequences of murine Snail, E-cadherin, Vimentin, or Fibronectin.

Microarray Analysis of MTB/TAN Tumors: Six primary and six recurrent MTB/TAN tumors were profiled on MGU74A version 2 oligonucleotide microarrays (Affymetrix®, South San Francisco, Calif.) per manufacturer's instructions. Data were analyzed and compared for significant gene expression changes as previously described (Master et al., *Genome Biology.* 6:R20, 2005 (2004)).

Tumor Grafting: Chronically induced tumor-bearing MTB/TAN animals were sacrificed by $CO_2$ asphyxiation. Primary tumors were harvested and chilled on ice in DMEM (Cellgro®, Mediatech Inc., Herndon, Va.) prior to being grafted subcutaneously onto the flanks of anesthetized recipient animals. Recipient animals were then placed on doxycycline treatment, and graft outgrowths were biopsied when they reached a size of approximately 15×15 mm$^2$. Grafted animals were maintained on doxycycline after biopsy to document continued graft growth, at which time doxycycline was withdrawn, and the regression/recurrence behavior of the grafts was monitored.

Tumor Cell Culture: Tumors were harvested from mice at the time of sacrifice, weighed, and diced into small pieces with sterile razor blades. Tumor pieces were rotated for 30 minutes at 37° C. in 10 ml/g solution of 1 mg/ml collagenase (Worthington Biochemical Co., Lakewood, N.J.), 1 mg/ml fatty-acid-free BSA (Sigma-Aldrich Co., St. Louis, Mo.), and 100 units/milliliter (u/ml) each penicillin and streptomycin (Invitrogen GIBCO®, Carlsbad, Calif.) in DMEM (Cellgro®, Mediatech Inc., Herndon, Va.). Tumor cells were triturated and 0.5 ml (0.05 g tumor) was plated onto 10 cm tissue culture plates. Cells were grown in DMEM supplemented with 10% calf serum, 4 mM L-glutamine (Invitrogen GIBCO®, Carlsbad, Calif.), 100 u/ml penicillin (Invitrogen GIBCO®, Carlsbad, Calif.), 100 u/ml streptomycin (Invitrogen GIBCO®, Carlsbad, Calif.), 5 μg/ml insulin (Sigma-Aldrich Co., St. Louis, Mo.), 10 μg/ml EGF (Sigma-Aldrich Co., St. Louis, Mo.), 1 μg/ml hydrocortisone (Sigma-Aldrich Co., St. Louis, Mo.), 1 μM progesterone (Sigma-Aldrich Co., St. Louis, Mo.), 5 μg/ml prolactin (National Hormone Peptide Program, Harbor-UCLA Medical Center, Torrance, Calif.), and 2 μg/ml doxycycline (Sigma-Aldrich Co., St. Louis, Mo.).

Tumor Cell Infections: Ten μg of pk1 or pk1-Snail were transfected by calcium chloride transfection into BOSC packaging cells, along with 5 μg each of pEGFP (BD Biosciences Clontech, Mountain View, Calif.), pCGP (gag-pol) and pHIT123 (ecotropic env). After 6 hours, cells were washed with 1×PBS and fed with tumor growth media (DMEM supplemented with 10% calf serum, 4 mM L-glutamine, 100 u/ml penicillin, 100 u/ml streptomycin, 5 μg/ml insulin, 10 μg/ml EGF, 1 μg/ml hydrocortisone, 1 μM progesterone, 5 μg/ml prolactin, and 2 μg/ml doxycycline). Twenty-four hours later, transfection efficiency was confirmed by EGFP expression, and supernatants were collected, snap frozen, and stored −80° C.

For primary tumor cell infections, cells were plated in 6-well plates, and 1 ml of viral supernatant (pk1 or pk1-Snail) plus 16 μg/ml Polybrene® (Sigma-Aldrich Co., St. Louis, Mo.) were added. Eight hours later, 1 ml of tumor growth media (see above) was added, and cells were incubated overnight. The following day, the cells were split into 60 mm plates and re-fed. When cells reached 50-70% confluence, selection for transduced cells was begun by addition of 2 µg/ml puromycin.

Tumor Cell Injections: Pk1 or pk1-Snail transduced cells were trypsinized, spun 5 minutes at 1000 rpm, resuspended in tumor growth media plus puromycin, and counted for live cells by trypan blue exclusion on a hemacytometer. Cells were resuspended at a concentration of $2\times10^7$ cells/ml in tumor growth media plus puromycin and maintained on ice during transit to the animal facility. Recipient nude mice that had been pre-treated with 2 mg/ml doxycycline in their drinking water for 1 week were injected on each flank with $2\times10^6$ cells per injection site. Mice were monitored weekly for tumor development.

Human Breast Cancer Data Sets

Data Set Descriptions cRNA was made by pooling equal amounts of cRNA from each of the sporadic breast cancer samples. Microarray data were available as background-corrected and normalized $\log_{10}$ ratios of the two channels. Only the 97 sporadic tumor samples were used in the analyses. Snail expression data was missing in one of the 97 samples.

Sorlie et al.: The Sorlie data set consists of 122 samples, 87 of which were sampled as part of two independent prospective studies investigating response to chemotherapy in locally advanced breast cancer (55 from patients treated with doxorubicin monotherapy, 32 from patients treated with 5-fluorouracil and mitomycin C; Sorlie et al., supra (2003)). Thirteen of the 87 patients had distant metastasis (presumably at diagnosis). The remaining 35 samples include 3 metastases (2 lymph node and one ovary), 4 normal breast samples and 28 primary tumor specimens collected either at Stanford or in Norway. Samples were analyzed on two-color spotted cDNA microarrays from 9 different batches, with array sizes ranging from approximately 8,800 to 44,000 features (8164 features are common to all the arrays). Common reference mRNA was made from an equal mixture of 11 established human cell lines. Microarray data were available as background-corrected and normalized $\log_2$ ratios of the two channels. Only the 74 samples with no distant metastasis (from the two prospective studies) were used in the analyses. Due to differences in the arrays used, Snail expression analysis was available in only 24 of the 74 samples. Among these 24 samples, two were from patients with zero recurrence-free survival time and were, therefore, excluded from survival analyses.

Ma et al.: The Ma data set consists of 60 hormone receptor-positive (59 estrogen receptor-positive) breast tumor samples from patients subsequently treated with adjuvant tamoxifen. Samples were analyzed on two-color spotted oligonucleotide microarrays containing approximately 22,000 features (Ma et al., supra (2004)). Universal Human Reference total RNA was used as the common reference. Microarray data were available as normalized log2 ratios of the two channels. All 60 samples were used in the analyses.

Wang et al.: The Wang data set consists of samples from 286 patients with lymph-node-negative breast cancer, 219 of which had undergone breast-conserving surgery and 67 modified radical mastectomy (Wang et al., supra (2005)). 248 patients received radiotherapy. None of the patients received systemic neoadjuvant or adjuvant therapy. Samples were analyzed on Affymetrix U133A GeneChip oligonucleotide microarrays containing approximately 22,000 probe sets. All samples were used in the analyses.

Data Analysis

Survival analysis: The association between Snail expression and recurrence-free survival (RFS) time within 5 years of diagnosis was analyzed using the follow-up outcome data available for each data set. Samples in the van't Veer, Sorlie and Ma data sets were separated into three equal-sized groups according to Snail expression. The probability of RFS over time for each group was calculated using the Kaplan-Meier estimator. The two groups with higher Snail expression in both the van't Veer and the Sorlie data sets were merged because of the significant overlap of their survival curves. The two groups with lower Snail expression in the Ma data set were merged for the same reason. For the Wang data set, samples were separated into two groups based on MAS5 absolute expression analysis p-values of the Snail probe set using default values, such that the high Snail group consisted of samples considered by MAS5 to be present or marginally present and the low Snail group consisted of samples considered by MAS5 to be absent. The survival curves for the resulting two groups were compared using the log-rank test.

Hazard ratios of recurrence-free survival between the Snail groups were estimated using the Cox proportional hazards model. Hazard ratios were also calculated for prognostic indicators, including tumor size, tumor grade, lymph node status, ER status and HER2 status. For tumor size analysis, samples in both the van't Veer and the Ma data sets were separated into three size groups: <1.5 cm, 1.5 cm-2.5 cm and >2.5 cm. Samples in the Sorlie data set were separated into two groups: $\leq$3 cm and >3 cm. Tumor size information was not available for the Wang data set.

Association Between Snail Expression and Prognostic Indicators:

Tumor size: Tumor size data were available for all data sets except Wang. Contingency tables of Snail expression groups versus tumor size groups were analyzed by Fisher's exact test. The difference in Snail expression as a continuous variable among the size groups and the difference in tumor diameter as a continuous variable between the high and low Snail groups were both tested by ANOVA. The significance of the correlation between Snail expression and tumor diameter, both as continuous variables, was assessed by the p-value of the Pearson correlation coefficient.

Tumor grade: Tumor grade data were available for all data sets except Wang. Both the van't Veer and the Sorlie data sets were analyzed using three grade groups (1, 2 and 3), while the grade 1 group in the Ma data set consisted of only three samples and was thus merged with the grade 2 group in the analyses. Contingency tables of Snail expression groups versus tumor grade groups were analyzed by Fisher's exact test. The difference in Snail expression as a continuous variable among the grade groups was tested by ANOVA.

Lymph node status: Lymph node status data were available for the Sorlie and Ma data sets. Contingency tables of Snail expression groups versus lymph node status were analyzed by Fisher's exact test. The difference in Snail expression as a continuous variable between lymph node positive and negative samples was tested by ANOVA.

ER status: ER status data were available for all four data sets. Contingency tables of Snail expression groups versus ER status were analyzed by Fisher's exact test. The difference in Snail expression as a continuous variable between ER positive and negative samples, was tested by ANOVA. The difference in ESR1 expression as a continuous variable between high and low Snail samples was also tested by ANOVA. The significance of the correlation between Snail expression and ESR1 expression, both as continuous variables, in ER positive samples, ER negative samples, or all samples, was assessed by the p-value of the Pearson correlation coefficient.

HER2 status: HER2 status, as determined by immunohistochemistry, was available for the Ma data set. The Sorlie clustering algorithm of gene expression data identified an ERBB2+ group of samples, which were used equivalently as a HER2 positive grouping in the analyses of the Sorlie data set (Sorlie et al., *Proc. Natl. Acad. Sci. USA* 98:10869-10874 (2001)). For the van't Veer data set, samples were grouped as HER2-positive if the expression level of HER2 was above 0 (expressed as a log2 ratio) and HER2-negative if the expression level was below 0. A similar criterion was used to assign HER2 status to the Wang samples with the exception that the cutoff was set at 0.5 for the log2 ratio to mean expression, which is near the minimum between the two peaks of the bimodal distribution of HER2 expression. Contingency tables of Snail expression groups versus HER2 status were analyzed by Fisher's exact test. The difference in Snail expression, as a continuous variable between HER2 positive and negative samples, was tested by ANOVA. The difference in HER2 expression, as a continuous variable between high and low Snail samples, was also tested by ANOVA. The significance of the correlation between Snail expression and HER2 expression, both as continuous variables, was assessed by the p-value of the Pearson correlation coefficient.

Tumor histology types: Tumor histology data were available for the Sorlie and the Ma data sets. Tumor types other than ductal or lobular in the Sorlie data set were excluded from the analyses because these constituted a small proportion of the total. Tumor types in the Ma data set include ductal, lobular, and a mixture of ductal and lobular features. Contingency tables of Snail expression groups versus tumor histological types were analyzed by Fisher's exact test. The difference in Snail expression, as a continuous variable among the tumor types, was tested by ANOVA.

Tumor subtypes: Sorlie et al. previously categorized tumors within their own data set and within the van't Veer data set into five tumor subtypes: Basal, Luminal A, Luminal B, ERBB2+, and Normal breast-like (Sorlie et al., supra (2001)). Contingency tables of Snail expression groups versus tumor subtypes were analyzed by Fisher's exact test. The difference in Snail expression as a continuous variable among the tumor subtypes was tested by ANOVA.

Hazard Ratios:

Hazard ratios of recurrence-free survival between the Snail expression groups were estimated using the Cox proportional hazards regression. The same analysis was also used to analyze the association of recurrence-free survival with various prognostic indicators, including tumor size group, tumor grade, lymph node status, ER status and HER2 status. Samples in both the van't Veer and the Ma data set were separated into three size groups: <1.5 cm, 1.5 cm-2.5 cm and >2.5 cm. Samples in the Sorlie data set were separated into two groups: ≦3 cm and >3 cm. Each prognostic indicator having a significant univariate effect on survival was added in the Snail-only model as a second independent variable to assess the effect of Snail expression on survival adjusted for the prognostic indicator.

Example 1

Fully Regressed Neu-Induced Tumors Recur Spontaneously Following a Period of Dormancy A doxycycline-inducible, bitransgenic mouse model for HER-2/neu-induced mammary carcinogenesis, referred to as MMTV-rtTA/TetO-NeuNT (MTB/TAN), has been previously generated, see Gunther et al., *FASEB J.* 16:283-292 (2002). These mice express the reverse tetracycline-dependent transactivator (rtTA) in mammary epithelial cells, under the control the mouse mammary tumor virus promoter/enhancer, and an activated form of the neu receptor tyrosine kinase, under the control of the tet operator. When neu expression is induced with doxycycline, MTB/TAN mice develop multiple invasive mammary adenocarcinomas, many of which metastasize to the lung (Moody et al., supra (2002)). Notably, down-regulation of neu expression in the vast majority of these fully formed mammary tumors results in their regression to a non-palpable state. However, following a period of dormancy, some mice bearing fully regressed tumors, eventually develop spontaneous tumor recurrences in the absence of neu expression.

To investigate the mechanisms responsible for the recurrence of neu-induced mammary tumors, a large cohort of tumor-bearing mice was first generated. Of 507 neu-induced primary mammary tumors monitored in 62 MTB/TAN mice, 493 (97%) regressed to a non-palpable state following doxycycline withdrawal and down-regulation of the neu pathway. Two neu-induced primary tumors failed to regress at all following doxycycline withdrawal, whereas an additional 11 primary tumors regressed partially and then rapidly resumed neu-independent growth in the absence of doxycycline. Thus, in nearly all cases, the vast majority of cells within neu-induced primary tumors remain dependent upon Neu for maintenance of the transformed state.

Fifty mice in which all tumors had regressed to a non-palpable state following doxycycline withdrawal were monitored for extended periods of time in the absence of doxycycline treatment. Over a one-year period, 43 (86%) of these mice spontaneously developed recurrent tumors in the absence of doxycycline with a mean latency of 117 days (SD 48, range 27-222) (FIG. 1A). Formally, doxycycline-independent tumors arising in mice that had previously harbored mammary tumors could represent either genuine recurrences of neu-initiated tumors or the de novo formation of tumors in the absence of doxycycline treatment. The repeated observations that uninduced MTB/TAN animals do not develop tumors, even over periods exceeding 18 months, and that recurrent tumors always appear at a site at which a primary tumor had previously existed, each support that these doxycycline-independent tumors represent bona fide recurrences.

To confirm that doxycycline-independent recurrent tumors arise from cells within the original primary tumor, small fragments of primary tumors from MTB/TAN mice were implanted onto the flanks of wild-type mice. Grafted hosts were initially maintained on doxycycline to permit tumor outgrowth, after which time, doxycycline was withdrawn. Similar to the behavior of primary mammary tumors in MTB/TAN mice, grafted tumors regressed to a non-palpable state following doxycycline withdrawal, and a subset of these regressed tumor grafts eventually recurred at the original site following a latent period. Since tumors in non-transgenic hosts could only arise from grafted cells, these data confirm that doxycycline-independent tumors that arise in MTB/TAN mice harboring fully regressed tumors are, in fact, recurrences derived from cells within the primary tumor. This conclusion is further strengthened by the subsequent demonstration that epithelial cell cultures derived from primary neu-induced mammary tumors also give rise to recurrences when subjected to a similar grafting protocol (see below).

Analysis of mammary tumor behavior in individual intact MTB/TAN mice revealed that recurrent tumors arose stochastically over an eight-month period, frequently following a prolonged latency period (FIG. 1B). The concept of tumor latency arose as a result of the inability of continuous growth models to explain the kinetics of tumor recurrence in patients, as well as the lack of a relationship between the length of time from surgery to tumor recurrence and the growth rate of tumors once they reappear. Analogous to this, the latency of tumor recurrence in MTB/TAN mice was considerably longer than that observed for primary tumor development following neu induction (mean latency 117 vs. 42 days, respectively; FIG. 1A and Moody et al., supra (2002)). Similarly, the growth rate of recurrent tumors once they reappeared was unrelated to the length of time between tumor regression and tumor recurrence (FIG. 1B). Thus, as with breast cancer patients, the timing of tumor recurrence and kinetics of recurrent tumor growth cannot be explained by a model postulating constant growth of residual tumor cells. In aggregate, therefore, these observations show that de-induced MTB/TAN mice harbor residual neoplastic cells at the sites of their original tumors that persist in a latent state for variable periods of time before re-emerging as recurrent disease.

Example 2

Fully Regressed Neu-Induced Tumors Recur in the Absence of Neu Expression

Figure 2A:
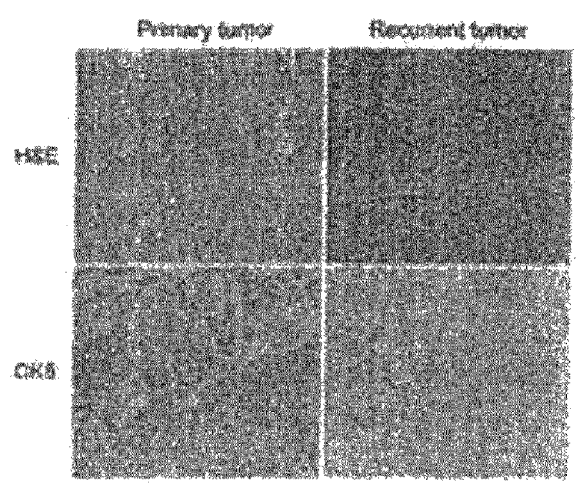
FIGS. 2A-2C are images of hematoxylin and eosin (H&E) and anti-Cytokeratin 8 (CK8) stained sections from representative MTB/TAN primary, neu-expressing and MTB/TAN recurrent, neu-negative tumors.
Figure 2B:
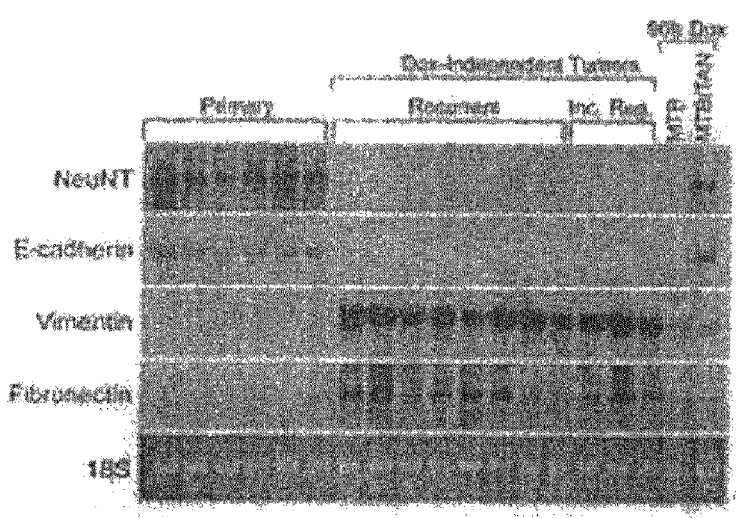

In theory, doxycycline-independent tumor recurrences could result from doxycycline-independent activation of the NeuNT transgene, compensatory up-regulation of endogenous ErbB2, or activation of neu-independent growth and/or survival pathways. Since the TetO-NeuNT transgene also contains a bicistronic IRES-firefly luciferase cassette, transgene expression may be monitored longitudinally in mice by non-invasive in vivo imaging of luciferase. Accordingly, luciferase activity was readily visualized within primary tumors in MTB/TAN mice maintained on doxycycline, whereas mice maintained off doxycycline, harboring either fully regressed or recurrent tumors, did not express detectable luciferase activity (FIG. 1C). In addition, Northern analysis, as well as anti-ErbB2 immunohistochemistry, failed to detect up-regulation of endogenous ErbB2 in recurrent tumors (FIG. 2B and data not shown). These observations indicate that spontaneous recurrence of neu-induced mammary tumors occurs by a process other than the doxycycline-independent reactivation of the NeuNT transgene or compensatory up-regulation of endogenous ErbB2.

Taken together, these findings demonstrate that a subset of cells within neu-induced primary tumors are ultimately capable of progressing to a state that is independent of neu overexpression for survival and growth. Furthermore, the fact that MTB/TAN mice bearing fully regressed tumors typically experience recurrence following a period of latency of up to eight months in duration, indicates that most mice bearing fully regressed tumors harbor viable residual neoplastic cells that persist in the mammary gland for extended periods of time.

Example 3

Recurrent Tumors have Characteristics of Epithelial-to-Mesenchymal Transition

As previously described, neu-induced mammary adenocarcinomas in MTB/TAN mice maintained on doxycycline display a characteristic epithelial morphology and stain positively for the luminal epithelial marker, cytokeratin 8 (CK8) (Moody et al., supra, 2002). Since mammary tumors induced in mice by different oncogenic pathways have been shown to exhibit distinct, recognizable histopathological "signatures," it was reasoned that doxycycline-independent tumor recurrences that no longer expressed neu might not exhibit the classic neu phenotype (Cardiff et al., Oncogene 19:968-988 (2000); Cardiff et al., Amer. J. Pathol. 139:495-501 (1991)). In agreement with this prediction, histopathological examination of multiple neu-negative, doxycycline-independent recurrent tumors revealed that the vast majority of these tumors were composed of spindle-shaped cells with mesenchymal morphology (FIG. 2A). Furthermore, immunohistochemical analysis demonstrated that recurrent tumors had down-regulated CK8, although occasional CK8-positive cells were detected (FIG. 2A).

Figure 2C:
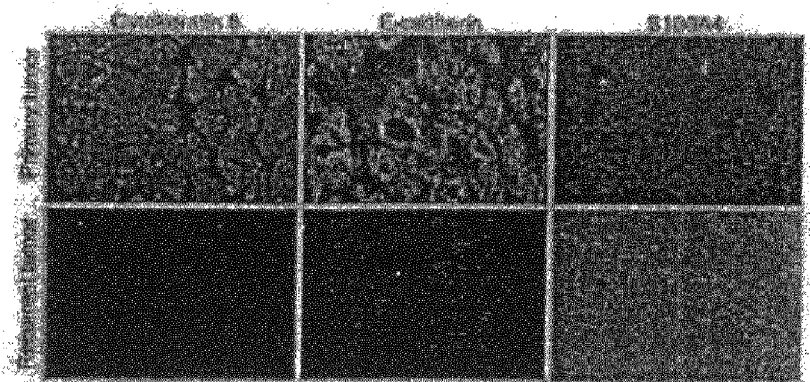
Figures 3A, 3B, 3C, 3D:
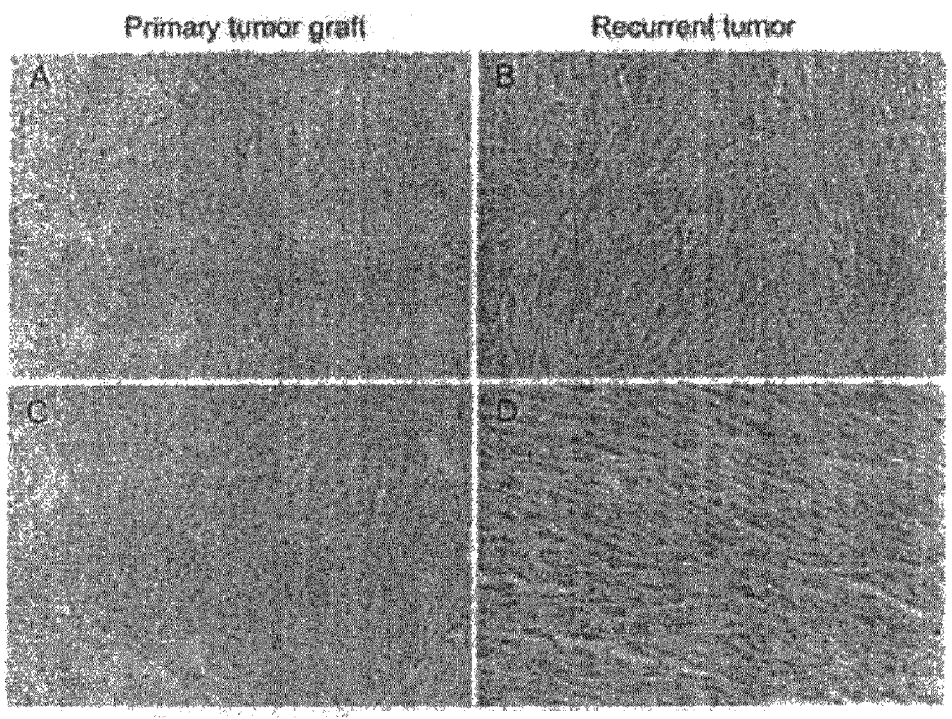
FIGS. 3A-3D depict hematoxylin and eosin stained sections of tumors.

As a result of the above findings, a hypothesis that that neu-induced mammary tumors undergo epithelial-to-mesenchymal transition (EMT) prior to their re-emergence as neu-independent recurrent tumors was developed and tested. Consistent with this hypothesis, Northern analysis confirmed the absence of NeuNT transgene expression in recurrent tumors and further revealed that expression of the mesenchymal markers vimentin and fibronectin was up-regulated (FIG. 2B). Conversely, a striking reduction in expression of the epithelial marker E-cadherin was observed in virtually every neu-independent recurrent tumor (FIG. 2B). E-cadherin is an essential component of adherens junctions in epithelial cells and is one of the markers whose expression is commonly lost in EMT. Immunofluorescence studies confirmed that recurrent tumors down-regulate expression of CK8 and E-cadherin and up-regulate expression of the mesenchymal marker, S100A4 (fibroblast-specific protein, Fsp1) (FIG. 2C). These findings demonstrate that recurrent tumors display multiple characteristic features of cells that have undergone EMT.

Example 4

Mesenchymal Recurrences Arise from Primary Epithelial Tumors

Since primary neu-dependent mammary tumors and doxycycline-independent tumor recurrences exhibit strikingly different morphological phenotypes, experiments were designed to confirm that mesenchymal recurrences arise from primary epithelial tumors. Two lines of evidence indicate that this is indeed the case. First, both Northern and histological analysis were performed on the small number of primary neu-induced mammary tumors that regressed only partially following doxycycline withdrawal before resuming growth. These analyses revealed that incompletely-regressing, doxycycline-independent primary tumors, which remain clinically apparent throughout their period of regression and re-growth, display the same spindle cell phenotype and identical molecular characteristics, with respect to markers of EMT, as doxycycline-independent recurrences (FIG. 2B and data not shown). This indicates that some or all of the same cellular processes that lead to tumor recurrence also contribute to the development of neu-independent primary tumors. As such, this observation adds further credence to the conclusion that spindle-cell tumors arise from epithelial cells within primary tumors, rather than from de novo transformation of a mesenchymal cell type.

Secondly, primary MTB/TAN tumors grafted onto the flanks of wild-type mice were allowed to engraft and grow on doxycycline before being induced to regress to a non-palpable state by withdrawal of doxycycline treatment. Grafted mice bearing fully regressed tumors were monitored for spontaneous recurrence in the absence of doxycycline. Primary tumor grafts were biopsied prior to doxycycline withdrawal, and doxycycline-independent tumors that eventually recurred at graft sites were harvested. Histological analysis of these matched sets of primary and recurrent tumor grafts demonstrated that primary tumor grafts displayed the classic neu epithelial phenotype, whereas doxycycline-independent recurrences that arose at the same sites had acquired a mesenchymal phenotype (FIGS. 3A-D). Taken together, these two lines of evidence argue strongly that mesenchymal-appearing, doxycycline-independent tumors that arise at the site of fully regressed neu-induced neoplasms constitute recurrences of epithelial tumors that have undergone EMT.

Example 5

Snail, an Inducer of EMT, is Up-Regulated in Recurrent Neu-Induced Mammary Tumors A major regulator of EMT during embryonic mesoderm and neural crest development is the zinc finger transcription factor, Snail. First identified in *Drosophila* mutant embryos exhibiting defective mesoderm invagination, Snail has also been shown to be required for normal mesoderm development in mice (Grau et al., *Genetics.* 108:347-360 (1984); Carver et al., *Mol. Cell. Biol.* 21:8184-8188 (2001)). In addition to its role in EMT during normal mesoderm development, Snail has been shown to directly repress E-cadherin transcription in both mouse and human epithelial cell lines (Batlle et al., *Nat. Cell Biol.* 2:84-89 (2000); Cano et al., *Nat Cell Biol.* 2:76-83 (2000)). Consistent with this, invasive ductal carcinomas of the breast have been reported to express Snail in a manner that is inversely correlated with E-cadherin expression (Cheng et al., *Oncogene* 20:3814-3823 (2001)). Moreover, both Snail and its closely related family member Slug have been shown to repress endogenous E-cadherin expression in human breast cancer cell lines (Hajra et al., *Cancer Res.* 62:1613-1618 (2002)).

In light of the known association of Snail with EMT, Snail expression in recurrent, neu-induced mammary tumors that exhibited features of EMT was examined. Microarray analysis of doxycycline-independent MTB/TAN tumors demonstrated a 9-fold increase in Snail expression compared to primary MTB/TAN tumors ($p=8\times10^{-6}$), whereas only a 1.8-fold change in expression was detected in its closely related family member, Slug ($p=10^{-4}$) (FIG. 4A). Northern analysis confirmed that recurrent tumors express increased levels of Snail compared to primary tumors (FIG. 4B). Similarly, consistent with their spindle-cell appearance, primary mammary tumors that regressed only partially prior to resuming growth in a neu- and doxycycline-independent manner also displayed increased levels of Snail (FIG. 4B).

Example 6

Snail Induces EMT in Primary Neu-Induced Tumor Cells In Vitro

Since it had been observed a correlation between Snail expression and acquisition of a mesenchymal phenotype in doxycycline-independent tumors, experiments were designed to test whether Snail could induce primary neu-induced mammary tumor cells to undergo EMT. Although several studies in epithelial cell lines have demonstrated that Snail expression may induce EMT, some normal and malignant epithelial cell lines have proven to be resistant to this phenomenon in vitro (Batlle et al., supra (2000); Cano et al., supra (2000); Vincent-Salomon et al., *Breast Cancer Res.*

Figures 5A, 5B, 5C:
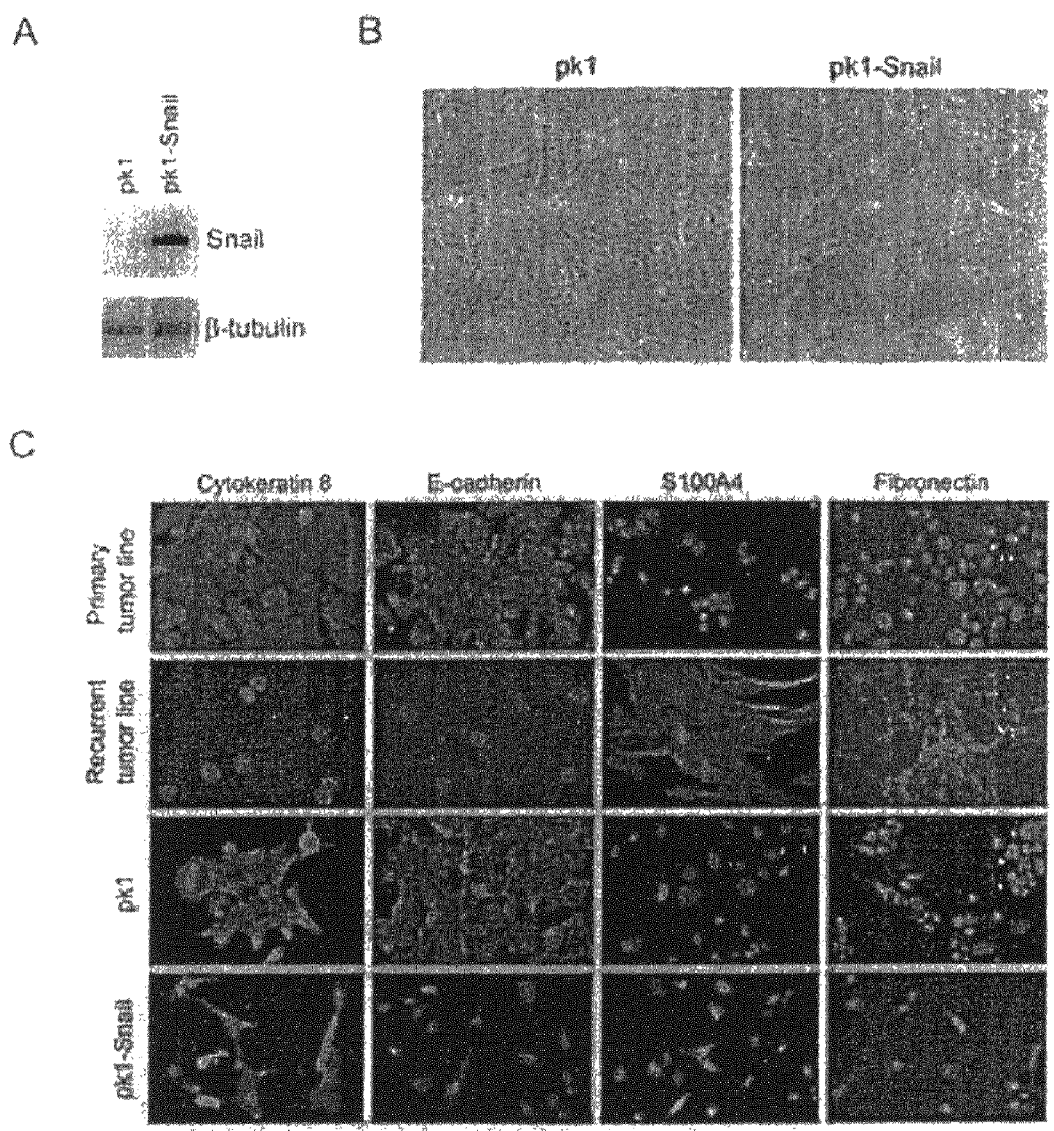
FIGS. 5A-5C show that Snail expression in neu-induced primary tumor cells is sufficient to induce the acquisition of a spindle-shaped morphology.

5:101-106 (2003)). Therefore, to determine whether Snail is capable of inducing EMT in neu-expressing tumor cells, primary tumor cells maintained on doxycycline were transduced with a retroviral vector encoding Snail or with the control retroviral vector, pk1. Infected cells were selected in puromycin-containing media, and immunoblotting was performed to assess Snail expression in transduced cells (FIG. 5A). Within two weeks of transduction, pk1-Snail-infected cells acquired a fibroblastic spindle cell phenotype accompanied by loss of cell-to-cell contacts (FIG. 5B). In contrast, pk1-infected control cells retained their epithelial morphology. These results demonstrate that Snail expression in neu-induced primary tumor cells is sufficient to induce the acquisition of a spindle-shaped morphology.

Since the transition to a spindle-shaped morphology is consistent with EMT, alterations associated with EMT were also examined at the molecular level. Primary tumor cells transduced with pk1- or pk1-Snail expressing retroviral vectors, as well as non-transduced primary and recurrent tumor cells, were immunostained with antibodies directed against the epithelial cell markers CK8 and E-cadherin, as well as the mesenchymal markers, S100A4 and fibronectin. As expected, CK8 and E-cadherin were expressed in both uninfected and pk1-infected primary tumor cells, whereas expression of these epithelial markers was lost in cells cultured from recurrent tumors (FIG. 5C). Conversely, the mesenchymal markers, S100A4 and fibronectin, were highly up-regulated in the recurrent tumor cell line compared to uninfected or pk1-infected primary tumor cells.

Notably, while complete repression of E-cadherin expression was observed in primary tumor cells transduced with pk1-Snail, CK8 expression was lost in only a fraction of Snail-expressing primary tumor cells (FIG. 5C). Similarly, a marked increase in S100A4 and fibronectin expression was evident in a subset of pk1-Snail-infected primary tumor cells (FIG. 5C). The up-regulation of mesenchymal markers in only a subset of Snail-transduced cells contrasts with the ubiquitous up-regulation of mesenchymal markers in recurrent tumor cells. This differential behavior may be due to the concurrent expression of neu in tumor cell lines maintained on doxycycline, since neu may impede Snail's ability to induce the full expression of EMT markers. Alternately, full manifestation of the EMT phenotype may require additional genetic or epigenetic alterations besides Snail expression. Nonetheless, complete transition to a mesenchymal morphology occurs in pk1-Snail infected cells. In aggregate, these observations demonstrate that Snail expression triggers a mesenchymal phenotype in neu-induced primary tumor cells, as indicated by morphological changes, the concomitant loss of E-cadherin expression, and the induction of mesenchymal markers associated with EMT.

Example 7

Snail Promotes the Recurrence of Neu-Induced Primary Tumors

Figure 6A:
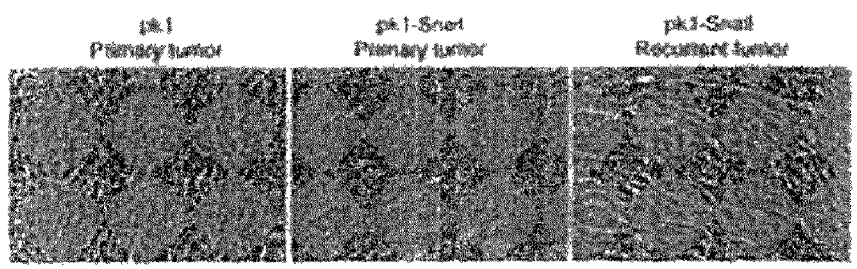
FIGS. 6A-6D show that Snail directly promotes tumor recurrence.
Figure 6B:
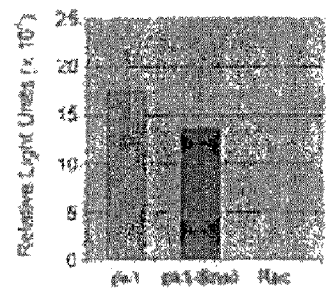

Since virtually all transgene-independent MTB/TAN recurrent tumors display a mesenchymal phenotype and express high levels of Snail, it was hypothesized that Snail may directly promote tumor recurrence. To investigate this possibility, pk1-Snail- or pk1-transduced primary tumor cells were grafted onto the flanks of nude mice maintained on doxycycline. Both sets of cells formed tumors with equal efficiency. As predicted, tumor grafts derived from pk1-transduced primary tumor cells displayed an epithelial morphology, whereas tumor grafts arising from pk1-Snail-transduced cells exhibited a mesenchymal morphology, despite continued expression of the neu oncogene (FIG. 6A). To confirm that tumors derived from pk1-Snail-transduced cells do not have altered NeuNT transgene expression prior to the withdrawal of doxycycline, luciferase activity levels were assayed in pk1 and pk1-Snail transduced tumor grafts harvested from mice maintained on doxycycline. As expected, in mice maintained on doxycycline, both pk1-Snail and pk1 tumor grafts expressed high, comparable levels of the NeuNT-IRES-Luciferase transgene (FIG. 6B).

Figure 6C:
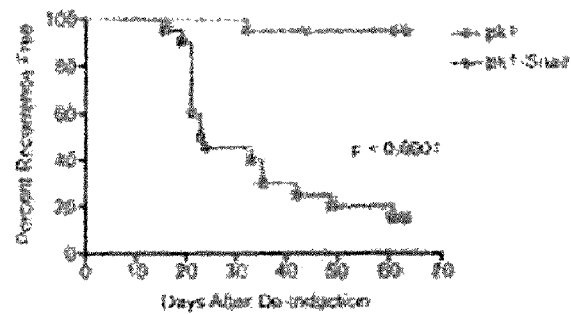

When pk1 and pk1-Snail-transduced tumor grafts reached a size of 3 mm$^3$, doxycycline was withdrawn from grafted mice. All tumors regressed to a non-palpable state following doxycycline withdrawal, regardless of Snail expression status. Strikingly, however, within 60 days of neu down-regulation, 17 of 20 (85%) pk1-Snail-transduced tumors recurred, whereas only 1 of 20 (5%) pk1-transduced tumors recurred (p<0.0001) (FIG. 6C). Moreover, similar to recurrent tumors that arose in tumor-bearing MTB/TAN mice withdrawn from doxycycline, regressed pk1-Snail tumor grafts that recurred in the absence of doxycycline lacked detectable NeuNT transgene expression (FIG. 6B).

Figure 6D:
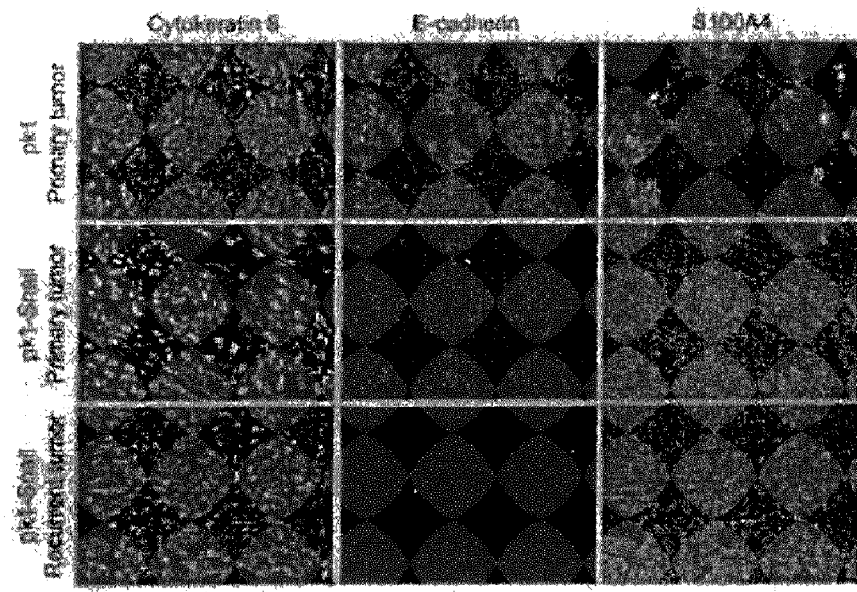

Notably, pk1-Snail-induced recurrent tumors displayed a fibroblastic phenotype similar both to doxycycline-independent tumor recurrences arising in MTB/TAN mice and to pk1-Snail-transduced primary tumor grafts arising in mice maintained on doxycycline (FIG. 6A). Consistent with this, immunofluorescence analysis revealed the down-regulation of E-cadherin expression and up-regulation of S100A4 in both doxycycline-dependent pk1-Snail primary tumor grafts and doxycycline-independent pk1-Snail recurrent tumor grafts (FIG. 6D). In contrast, high levels of E-cadherin and low levels of S100A4 were observed in epithelial-appearing pk1 tumor grafts growing in doxycycline-treated mice (FIG. 6D). Thus, Snail-induced recurrent tumors are morphologically and molecularly similar to MTB/TAN recurrent tumors that arise in intact mice in the absence of NeuNT transgene expression. In aggregate, these data demonstrate that Snail promotes the rapid recurrence of primary tumor cells in vivo following down-regulation of the neu pathway.

Example 8

Snail Expression Predicts Decreased Recurrence-Free Survival in Subjects with Breast Cancer The observation that enforced Snail expression in primary tumor cells promotes mammary tumor recurrence in mice raised the question of the role of Snail in the recurrence of breast cancers in humans. The expectation was that women with primary breast cancers expressing high levels of Snail would experience recurrence at a faster rate and with a higher probability than women whose breast cancers expressed lower levels of Snail. Therefore, four microarray expression data sets derived from primary human breast cancers, and in which both Snail expression levels and clinical outcome were reported, were examined. For each data set, tumor samples were classified as either high or low Snail expressers based on array hybridization levels. The relationship between Snail expression level and five-year recurrence-free survival was then determined.

Figures 7A, 7B, 7C, 7D:
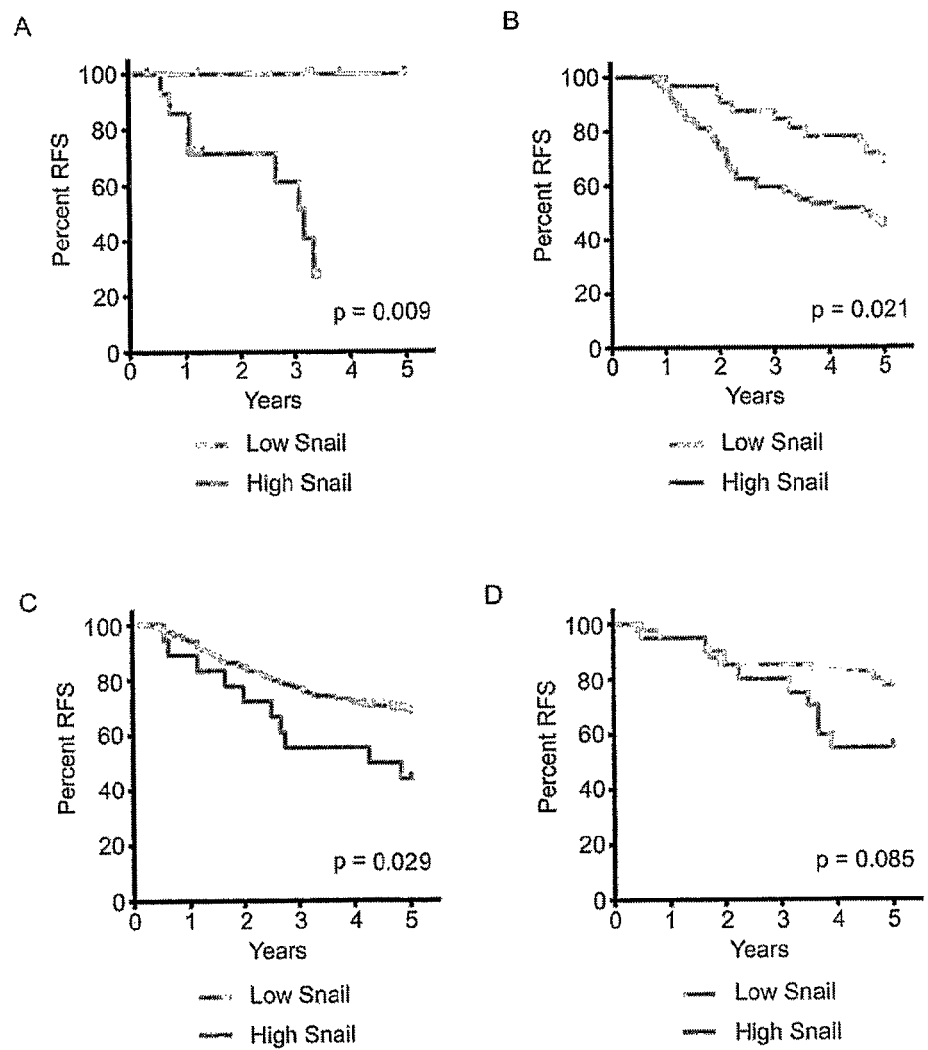
FIGS. 7A-7D present published 5-year survival information.

In the first series of samples examined, Sorlie et al. profiled 74 locally advanced estrogen receptor (ER)-positive and ER-negative primary breast cancers from patients without distant metastases at the time of presentation (Sorlie et al., *Proc Natl Acad Sci USA* 100:8418-8423 (2003)). Microarrays containing probe sets capable of detecting Snail had been used in analyzing 22 of these 74 samples. Applying the Kaplan-Meier estimator to high and low Snail expressing groups revealed a significant correlation between breast cancers expressing high levels of Snail and decreased recurrence-free survival (p=0.009) (FIG. 7A).

A similar analysis of recurrence-free survival was performed using microarray data derived from 97 ER-positive and ER-negative breast cancers that were lymph node-negative at presentation (van't Veer et al., supra (2002)). Similar to locally advanced tumors, high Snail expression in node-negative human primary breast cancers was significantly associated with decreased recurrence-free survival (p=0.021) (FIG. 7B). A third analysis of the relationship between Snail expression and the rate of distant recurrence in 286 patients with lymph node-negative breast cancers (Wang, et al., 2005) showed a similar significant association (p=0.029) between breast cancers expressing high levels of Snail and decreased recurrence-free survival (FIG. 7C). Finally, a set of 60 hormone receptor-positive breast cancers was analyzed from patients without distant metastases at the time of tumor resection (Ma et al., supra (2004)). A similar association between high Snail expression and rapid tumor recurrence was observed within this patient group, although the association did not reach significance (p=0.085) (FIG. 7D).

Taken together, these data demonstrate that high levels of Snail expression within human primary breast cancers predict decreased recurrence-free survival. The demonstration that four different Snail probes on four different microarray platforms applied to four different patient sample sets representing 464 patients each yield the same result, strongly suggests that the association between Snail expression and recurrence-free survival is not specific to the particular probes used to detect Snail, the particular platforms on which the microarray studies were performed, or the particular characteristics of the patient populations that were represented in these studies. Moreover, since a significant association between recurrence rate and Snail expression was observed for both locally-advanced and node-negative breast cancers, as well as among ER+ and ER– breast cancers, this analysis indicates that Snail expression will be an important prognostic indicator for breast cancer in a variety of clinical contexts.

Example 9

The Prognostic Significance of Snail Expression is Comparable to Classic Prognostic Indices Having determined that Snail expression levels predict recurrence-free survival in women with breast cancer, it is useful to determine the magnitude of this association compared to currently used clinical prognostic markers. Accordingly, the Cox proportional hazards regression was used to calculate hazard ratios (HR) for recurrence based on Snail expression, tumor size, tumor grade, lymph node status, ER status, and HER2 status (Table 1). This analysis revealed that the risk of breast cancer recurrence associated with high levels of Snail expression (HR>2-fold) is comparable to those associated with currently used clinical prognostic indicators, including that of ER status, tumor grade and lymph node status.

TABLE 1

Hazard Ratios For Recurrence Based on Clinical Prognostic Indicators

|  |  | Snail status | Tumor size | Tumor grade | LN status | ER status | HER2 status |
|---|---|---|---|---|---|---|---|
| Sorlie | HR | ** | 1.11 | 2.02* | 1.13 | 2.59* | 3.04* |
|  | 95% CI | ** | 0.49-0.51 | 1.13-3.59 | 0.59-3.03 | 1.16-5.79 | 1.04-8.86 |
|  | P-value | ** | 0.810 | 0.017 | 0.494 | 0.021 | 0.042 |
| van't Veer | HR | 2.24* | 1.73* | 3.01* | N/A | 2.32* | 4.10* |
|  | 95% CI | 1.11-4.53 | 1.19-2.53 | 1.60-5.68 | N/A | 1.28-4.19 | 1.72-9.80 |
|  | P-value | 0.025 | 0.004 | 0.001 | N/A | 0.005 | 0.002 |
| Wang | HR | 2.04* | N/A | N/A | N/A | 1.18 | 1.06 |
|  | 95% CI | 1.06-3.92 | N/A | N/A | N/A | 0.76-1.85 | 0.63-1.80 |
|  | P-value | 0.034 | N/A | N/A | N/A | 0.460 | 0.820 |
| Ma | HR | 2.21 | 1.33 | 2.01 | 0.97 | N/A | 1.90 |
|  | 95% CI | 0.87-5.57 | 0.80-2.23 | 0.94-4.30 | 0.44-2.14 | N/A | 0.45-8.13 |
|  | P-value | 0.094 | 0.269 | 0.073 | 0.947 | N/A | 0.385 |

Table 1: Hazard ratios, 95% confidence intervals, and p-values for breast cancer recurrence within 5 years of surgery, based on Snail expression grouping or previously described prognostic factors. Data are presented for each of the three human breast cancer data sets analyzed. HR = hazard ratio, CI = confidence interval, LN = lymph node. Statistically significant hazard ratios ($p < 0.05$) are marked with asterisks (*). The hazard ratio is mathematically infinite since no tumors with low Snail expression recurred. No confidence interval or p-value can be generated.

Example 10

Snail Predicts Recurrence-Free Survival, Independent of Other Prognostic Markers Since several prognostic markers have previously been established for human breast cancer, experiments were designed to determine whether the prognostic significance of Snail was simply attributable to its correlation with other markers of aggressive tumor behavior. The two characteristics of breast cancers in women that have been found to be the most robust predictors of recurrence-free survival are tumor size at diagnosis and lymph node status (Carter et al., supra (1989); Valagussa et al., supra (1978)). Therefore, the association between Snail expression and tumor size was analyzed by four methods: 1) contingency table analysis of binned Snail expression levels versus binned tumor size; 2) Snail expression level as a continuous variable versus binned tumor size; 3) binned Snail expression versus tumor size as a continuous variable; and 4) the correlation between Snail expression and tumor size in which each is analyzed as a continuous variable. None of these methods revealed a significant correlation between Snail expression and tumor size in any of the three human breast cancer data sets analyzed (Table 2).

Similarly, the correlation between Snail expression and lymph node status was examined using both contingency table analysis and Snail expression level as a continuous variable versus lymph node status. Again, neither of these methods revealed a significant correlation between Snail expression and lymph node status in either of the data sets analyzed (Table 2). Taken together, these findings indicate that Snail expression predicts recurrence-free survival independently of the two most commonly-used prognostic markers for breast cancer recurrence.

The association between Snail expression and other previously described prognostic indicators was then examined, including histological tumor grade, ER status, and HER2/neu expression (Esteva et al., Breast Cancer Res. 6:109-118 (2004); Schairer et al., J. Natl. Cancer Inst. 96:1311-1321 (2004); Berger et al., supra (1988); Slamon et al., supra (1987); Coradini et al., supra (2004)). Using analytical methods similar to those described above, no consistent association between Snail expression and any of these prognostic markers was detected (Table 2). Similarly, a correlation between Snail expression and HER2 expression was observed in only one of 16 such analyses. A statistically significant negative correlation between Snail expression and ER expression was detected in two of the four data sets.

TABLE 2

P-values for Association of Snail Expression with 5-Year Recurrence-Free Survival or Prognostic Indicators

| Recurrence-free survival | Analysis | Sorlie | van't Veer | Wang | Ma |
|---|---|---|---|---|---|
|  | Log-rank test based on Snail status | 0.009 * | 0.021 * | 0.029 * | 0.085 |
| Tumor size | Snail status vs. size status | 0.193 | 0.793 | N/A | 0.367 |
|  | Snail expression vs. size status | 0.397 | 0.686 | N/A | 0.533 |
|  | Snail status vs. size | 0.335 | 0.908 | N/A | 0.986 |
|  | Snail expression vs. size | 0.456 | 0.737 | N/A | 0.522 |
| Tumor grade | Snail status vs. grade status | 0.104 | 0.454 | N/A | 0.644 |
|  | Snail expression vs. grade status | 0.010* | 0.965 | N/A | 0.287 |
| Lymph node status | Snail status and lymph node status | 0.648 | N/A | N/A | 1.000 |
|  | Snail expression vs. lymph node status | 0.375 | N/A | N/A | 0.162 |
| ER status | Snail status vs. ER status | 1.000 | 0.636 | <0.0001* | N/A |
|  | Snail expression vs. ER status | 0.601 | 0.901 | 0.0002* | N/A |
|  | Snail status vs. ESR1 expression | 0.438 | 0.518 | <0.0001* | 0.024* |
|  | Snail expression vs. ESR1 expression | 0.146 | 0.806 | <0.0001* | 0.001* |
|  | Snail expression vs. ESR1 expression in ER$^+$ tumors | 0.166 | 0.258 | 0.0621 | <0.001* |
|  | Snail expression vs. ESR1 expression in ER$^-$ tumors | 0.784 | 0.475 | 0.0584 | N/A |

TABLE 2-continued

P-values for Association of Snail Expression with 5-Year Recurrence-Free Survival or Prognostic Indicators

| Recurrence-free survival | Analysis | Sorlie | van't Veer | Wang | Ma |
|---|---|---|---|---|---|
| | Log-rank test based on Snail status | 0.009 * | 0.021 * | 0.029 * | 0.085 |
| HER2 status | Snail status vs. HER2 status | 1.000 | 0.660 | 0.7482 | 0.272 |
| | Snail expression vs. HER2 status | 0.505 | 0.455 | 0.3850 | 0.095 |
| | Snail status vs. HER2 expression | 0.217 | 0.843 | 0.0353* | 0.707 |
| | Snail expression vs. HER2 expression | 0.373 | 0.933 | 0.1387 | 0.467 |
| Ductal vs lobular | Snail status vs. histological status | 1.000 | N/A | N/A | 1.000 |
| | Snail expression vs. histological status | 0.293 | N/A | N/A | 0.994 |
| Sorlie subtype classification | Snail status vs. Sorlie subtype status | 1.000 | 0.520 | N/A | N/A |
| | Snail expression vs. Sorlie subtype status | 0.334 | 0.976 | N/A | N/A |

Table 2: Correlation between Snail expression and 5-year recurrence-free survival, and between Snail expression and previously described prognostic factors for breast cancer. P-values are shown for each of the four human breast cancer data sets analyzed. "Status" designation refers to groupings of samples as described in Materials and Methods. All other designations refer to the variable as continuous, based either on microarray-determined expression levels or size. Contingency table analyses (group vs. group) were tested by Fisher's exact test. Group vs. continuous variable analyses were tested by ANOVA. Correlations between two continuous variables were tested by the p-value of the Pearson correlation coefficient. Statistically significant correlations ($p < 0.05$) are listed with asterisks (*).

Experiments were designed to determine whether Snail expression correlated with a specific cellular subtype of breast cancer that was associated with poor patient outcome. Sorlie et al. have previously described array-based methods for the molecular classification of human breast cancers into five subtypes: Luminal A, Luminal B+C, Basal, ERBB2+, and Normal breast-like (Sorlie et al., supra (2001)). Of these, the Basal and ERBB2+ subtypes were associated with the worst prognosis, whereas the Luminal A subtype has been associated with the best prognosis in both the Sorlie and van't Veer data sets. However, neither contingency table analysis nor continuous variable analysis of Snail expression differences between these subtypes revealed any correlation between Snail expression and tumor subtype classification (Table 2). Similarly, for the Sorlie and Ma data sets, information was provided regarding whether tumors were of ductal or lobular origin. However, neither researcher reported any correlation between Snail expression levels and ductal versus lobular tumor type in their respective data sets (Table 2). In aggregate, these results indicate that the ability of Snail expression levels to predict survival is not attributable to its preferential expression in a previously described aggressive breast cancer subtype.

Nevertheless, although Snail expression did not correlate with previously described prognostic markers, it was useful to determine whether adjusting for any of these factors would affect the ability of Snail expression to predict recurrence-free survival. Notably, the association between Snail expression and decreased recurrence-free survival remained statistically significant, even when adjusted individually for tumor grade, tumor size, ER status, or HER2 status (Table 3). Therefore, although limited correlations were observed between Snail expression and either tumor grade or HER2 status, in one data set each, and between Snail and ER status in two data sets, the correlation between elevated Snail expression and decreased recurrence-free survival is not attributable to any of these associations. Taken together, these findings indicate that Snail expression significantly predicts recurrence-free survival in women with breast cancer, and that this association is largely independent of previously described prognostic factors.

TABLE 3

Proportional Hazards Analyses of Snail Status and Selected Covariates

| | van't Veer | | | Wang | | |
|---|---|---|---|---|---|---|
| | HR | 95% CI | P-value | HR | 95% CI | P-value |
| Snail status | 2.09* | 1.03-4.24 | 0.040 | N/A | N/A | N/A |
| Tumor Grade | 1.51* | 1.51-5.33 | 0.001 | N/A | N/A | N/A |
| Snail status | 2.12* | 1.05-4.29 | 0.037 | N/A | N/A | N/A |
| Tumor Size | 1.70* | 1.16-2.49 | 0.006 | N/A | N/A | N/A |
| Snail status | 2.18* | 1.08-4.42 | 0.030 | 2.00 | 0.99-4.02 | 0.053 |
| ER status | 2.15* | 1.18-3.94 | 0.013 | 1.04 | 0.65-1.67 | 0.876 |
| Snail status | 2.06* | 1.01-4.19 | 0.046 | 2.07* | 1.07-4.00 | 0.031 |
| HER2 status | 3.68* | 1.53-8.86 | 0.004 | 1.12 | 0.66-1.89 | 0.687 |

Table 3. Proportional hazard ratios, confidence intervals, and p-values for 5-year recurrence free survival in the van't Veer et al. and Wang et al. data sets based on Snail expression groups controlled for tumor grade, tumor size, ER status, and HER2 status, and for each of these factors controlled for Snail expression. Statistically significant hazard ratios ($p < 0.05$) are listed with asterisks (*).

Thus, when combined, the inventive observations herein provide one of the first mechanistic insights into pathways that appear to contribute to breast cancer recurrence. In the case of Snail, there is now reason to move forward to develop drugs to inhibit this pathway for further testing. Nevertheless, its ability to predict recurrence-free survival in breast cancer patients, coupled with clear evidence that Snail promotes the recurrence of murine mammary tumors in vivo, emphasizes the potential clinical importance of this pathway. Snail, thus, represents an important new target for a generation of cancer therapeutics directed against specific molecules involved in breast cancer recurrence.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method for assessing risk of breast cancer recurrence in a subject previously diagnosed with breast cancer, but without diagnosis of metastatic or recurrent disease, the method comprising:
   obtaining a tissue sample of primary breast cancer from the subject;
   measuring expression of Snail in the sample;
   establishing a comparative standard level by measuring Snail expression in a pool of subjects without elevated Snail expression level, or selecting a previously established comparative standard level for such non-elevated Snail expression;
   comparing the level of Snail expression in the sample with the comparative standard;
   determining whether the level of measured expression of Snail in the sample is comparatively higher than the comparative standard; and
   predicting a higher risk of breast cancer recurrence in the subject based upon the comparatively higher level of expression of Snail in the sample.

2. The method of claim 1, wherein the determining step reveals whether the level of measured expression of Snail in the sample is lower than the comparative standard, and predicting a lower risk of breast cancer recurrence in the subject based upon the comparatively lower level of expression of Snail in the sample.

3. The method of claim 1, wherein the subject from which the breast cancer sample is obtained has a locally advanced breast cancer at the time of diagnosis.

4. The method of claim 1, wherein the subject from which the breast cancer sample is obtained is lymph-node negative for the cancer at the time of diagnosis.

5. The method of claim 1, wherein measuring expression of Snail in the sample further comprises detecting mRNA levels of Snail in the primary breast cancer.

6. The method of claim 1, further comprising assessing a second marker prognostic for breast cancer recurrence, wherein the second marker is selected from the group consisting of tumor size, tumor grade, ER status and HER2 status.

7. The method of claim 1, wherein in addition to measuring expression of Snail in the sample, the method further comprises determining the level of Snail expression in the subject's sampled tissue.

* * * * *